US012697019B2

(12) United States Patent
Cummings

(10) Patent No.: US 12,697,019 B2
(45) Date of Patent: Aug. 4, 2026

(54) REFILLABLE WATER RESERVOIR FOR AN ENDOSCOPE

(71) Applicant: Boston Scientific Scimed, Inc., Maple Grove, MN (US)

(72) Inventor: Nathan Thomas Cummings, Worcester, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 409 days.

(21) Appl. No.: 18/343,016

(22) Filed: Jun. 28, 2023

(65) Prior Publication Data

US 2024/0000305 A1     Jan. 4, 2024

Related U.S. Application Data

(60) Provisional application No. 63/356,701, filed on Jun. 29, 2022.

(51) Int. Cl.
| | |
|---|---|
| *A61B 1/00* | (2006.01) |
| *A61B 1/015* | (2006.01) |
| *A61B 1/12* | (2006.01) |

(52) U.S. Cl.
CPC .......... *A61B 1/126* (2013.01); *A61B 1/00119* (2013.01); *A61B 1/00128* (2013.01); *A61B 1/00131* (2013.01); *A61B 1/015* (2013.01)

(58) Field of Classification Search
None
See application file for complete search history.

(56) References Cited

U.S. PATENT DOCUMENTS

| | | |
|---|---|---|
| 5,836,364 A | 11/1998 | Burton |
| 11,246,471 B2 | 2/2022 | Grudo et al. |
| 11,576,566 B2 | 2/2023 | Pollock et al. |
| 2013/0105485 A1 | 5/2013 | Bork |
| 2019/0047754 A1 | 2/2019 | Dubiel et al. |
| 2021/0378487 A1 | 12/2021 | Lagow et al. |
| 2022/0192478 A1 | 6/2022 | Pollock et al. |
| 2022/0192479 A1 | 6/2022 | Harris et al. |

FOREIGN PATENT DOCUMENTS

CN         109665197 A       4/2019

OTHER PUBLICATIONS

International Search Report and Written Opinion dated Oct. 4, 2023 for International Application No. PCT/US2023/069230.

*Primary Examiner* — Levon J Shahinian
(74) *Attorney, Agent, or Firm* — Seager, Tufte & Wickhem, LLP

(57) ABSTRACT

Methods and systems for refilling a container during an endoscopic procedure. An illustrative container may comprise a container extending from a first end to a second end and having a reduced diameter stem extending from the first end, the reduced diameter stem defining an opening for receiving a fluid, a water outlet, a gas inlet, and a port. The port may comprise a sealing ring defining an aperture extending from a first end to a second of the sealing ring, the aperture in fluid communication with the opening in the container, a cap positioned adjacent to the first end of the aperture of the sealing ring, and a biasing mechanism disposed between the container and the sealing ring.

19 Claims, 8 Drawing Sheets

REFILLABLE WATER RESERVOIR FOR AN ENDOSCOPE

CROSS-REFERENCE TO RELATED APPLICATIONS

This application claims the benefit of U.S. Prov. Pat. App. No. 63/356,701, filed Jun. 29, 2022, titled REFILLABLE WATER RESERVOIR FOR AN ENDOSCOPE, which is incorporated herein by reference.

FIELD

This disclosure relates generally to medical fluid containers and methods, and particularly to a refillable container to supply fluid and/or gas to an endoscope.

BACKGROUND

Conventionally, endoscope devices have been widely used for performing diagnostic and/or therapeutic treatments. During endoscopic procedures, physicians may use a combination of air, irrigation and lens wash as a means of flushing debris, cleaning optics, and insufflating the working lumen. To enable these capabilities, compressed gasses from either the processor or alternative source are used to increase the pressure within a fluid bottle which either insufflates the working lumen or washes the lens of the endoscope. Additionally, a peristaltic pump can be used to irrigate the working lumen of debris. One of the challenges faced during endoscopic procedures is that the common water bottle and tube set used contain a maximum of 1 liter of water and are not designed to be refilled. This may force nurses/technicians to replace the water bottle multiple times a day. This may introduce multiple opportunities for contamination to the tube set by either contacting non-sterile surfaces or dropping the tubing on the floor.

It is with these considerations in mind that the improvements of the present disclosure may be useful.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary. Accordingly, while the disclosure is presented in terms of aspects or embodiments, it should be appreciated that individual aspects can be claimed separately or in combination with aspects and features of that embodiment or any other embodiment.

In a first example, a reservoir arranged and configured to couple to an endoscope for use in an endoscopic procedure may comprise a container configured to contain a fluid therein, the container extending from a first end to a second end and having a reduced diameter stem extending from the first end, the reduced diameter stem defining an opening for receiving a fluid, a water outlet, a gas inlet, and a port. The port may comprise a sealing ring defining an aperture extending from a first end to a second of the sealing ring, the aperture in fluid communication with the opening in the container, a cap positioned adjacent to the first end of the aperture of the sealing ring, and a biasing mechanism disposed between the container and the sealing ring.

Alternatively or additionally to any of the examples above, in another example, the water outlet may comprise a water supply tube including a first end, a second end, and a first lumen extending therethrough, wherein the first lumen is in fluid communication with a bottom portion of the container and the second end of the water supply tube is positioned external to the container and the gas inlet may comprise a gas supply tube including a first end, a second end, and a second lumen extending therethrough, wherein the second lumen is in operative fluid communication with the container and the second end of the gas supply tube is positioned external to the container.

Alternatively or additionally to any of the examples above, in another example, the biasing mechanism may be configured to bias the sealing ring away from the first end of the container.

Alternatively or additionally to any of the examples above, in another example, the sealing ring may be movable between a first configuration configured to fluidly seal the opening in the container and a second configuration configured to provide a fluid path from external to the container and through the aperture of the sealing ring and the opening in the container.

Alternatively or additionally to any of the examples above, in another example, when in the second configuration, the sealing ring may be pressed towards the first end of the container.

Alternatively or additionally to any of the examples above, in another example, the sealing ring may extend about at least a portion of the reduced diameter stem of the container.

Alternatively or additionally to any of the examples above, in another example, the cap may be held in a fixed orientation relative to the container.

Alternatively or additionally to any of the examples above, in another example, the reservoir may further comprise a tether extending between an interior of the container and the cap.

Alternatively or additionally to any of the examples above, in another example, the tether may comprise a first end coupled to the cap and a second end disposed within the interior of the container.

Alternatively or additionally to any of the examples above, in another example, the second end of the tether may be deformable between a first expanded configuration and a second collapsed configuration.

Alternatively or additionally to any of the examples above, in another example, when the second end of the tether is in the first expanded configuration, the second end of the of the tether may have a width greater than a width of the opening in the container.

Alternatively or additionally to any of the examples above, in another example, when the second end of the tether is in the second collapsed configuration, the second end of the of the tether may have a width less than a width of the opening in the container.

Alternatively or additionally to any of the examples above, in another example, the biasing mechanism may be configured to bias the sealing ring into the cap.

Alternatively or additionally to any of the examples above, in another example, a diameter of the aperture of the sealing ring may be substantially constant from the second end to an intermediate location and may increase from the intermediate location to the first end to form a tapered first end region.

Alternatively or additionally to any of the examples above, in another example, an outer diameter of the cap may be tapered and configured to mate with the tapered first end region of the aperture of the sealing ring.

Alternatively or additionally to any of the examples above, in another example, the reduced diameter stem may comprise a hollow cylindrical stem.

Alternatively or additionally to any of the examples above, in another example, the reservoir may further comprise an O-ring disposed between the sealing ring and the reduced diameter stem of the container.

Alternatively or additionally to any of the examples above, in another example, a system may comprise the reservoir of any one of the examples above and a filling bottle comprising a mouth, wherein the mouth may be configured to engage a surface of the sealing ring along a perimeter lying beyond an outermost extent of the cap.

In another example, a reservoir arranged and configured to couple to an endoscope for use in an endoscopic procedure may comprise a container configured to contain a fluid therein and having an inlet opening for receiving a fluid, a water outlet, a gas inlet, and a port. The port may comprise a housing comprising a reduced diameter stem defining an inlet opening in the housing for receiving a fluid, the housing further comprising an outlet opening, a sealing ring defining an aperture extending from a first end to a second of the sealing ring, the aperture in fluid communication with the inlet opening in the housing, a cap positioned adjacent to the first end of the aperture of the sealing ring, and a biasing mechanism disposed between the housing and the sealing ring. The reservoir may further comprise a flexible tubing line providing fluid communication between the outlet opening of the housing and the inlet opening of the container.

Alternatively or additionally to any of the examples above, in another example, the water outlet may comprise a water supply tube including a first end, a second end, and a first lumen extending therethrough, wherein the first lumen is in fluid communication with a bottom portion of the container and the second end of the water supply tube is positioned external to the container and the gas inlet may comprise a gas supply tube including a first end, a second end, and a second lumen extending therethrough, wherein the second lumen is in operative fluid communication with the container and the second end of the gas supply tube is positioned external to the container.

Alternatively or additionally to any of the examples above, in another example, the biasing mechanism may be configured to bias the sealing ring away from a first end of the housing.

Alternatively or additionally to any of the examples above, in another example, the sealing ring may be movable between a first configuration configured to fluidly seal the inlet opening in the housing and a second configuration configured to provide a fluid path from external to the housing and through the aperture of the sealing ring and the inlet opening in the housing.

Alternatively or additionally to any of the examples above, in another example, when in the second configuration, the sealing ring may be pressed towards the housing.

Alternatively or additionally to any of the examples above, in another example, the sealing ring may extend about at least a portion of the reduced diameter stem of the housing.

Alternatively or additionally to any of the examples above, in another example, the cap may be held in a fixed orientation relative to the housing.

Alternatively or additionally to any of the examples above, in another example, the reservoir may further comprise a tether extending between an interior of the housing and the cap.

Alternatively or additionally to any of the examples above, in another example, the tether may comprise a first end coupled to the cap and a second end disposed within the interior of the housing.

Alternatively or additionally to any of the examples above, in another example, the second end of the tether may be deformable between a first expanded configuration and a second collapsed configuration.

Alternatively or additionally to any of the examples above, in another example, when the second end of the tether is in the first expanded configuration, the second end of the of the tether may have a width greater than a width of the inlet opening in the housing.

Alternatively or additionally to any of the examples above, in another example, when the second end of the tether is in the second collapsed configuration, the second end of the of the tether may have a width less than a width of the inlet opening in the housing.

Alternatively or additionally to any of the examples above, in another example, the biasing mechanism may be configured to bias the sealing ring into the cap.

Alternatively or additionally to any of the examples above, in another example, a diameter of the aperture of the sealing ring may be substantially constant from the second end to an intermediate location and may increase from the intermediate location to the first end to form a tapered first end region.

Alternatively or additionally to any of the examples above, in another example, an outer diameter of the cap may be tapered and configured to mate with the tapered first end region of the aperture of the sealing ring.

Alternatively or additionally to any of the examples above, in another example, the reduced diameter stem may comprise a hollow cylindrical stem.

Alternatively or additionally to any of the examples above, in another example, the reservoir may further comprise an O-ring disposed between the sealing ring and the reduced diameter stem of the housing.

Alternatively or additionally to any of the examples above, in another example, a system may comprise the reservoir of any one of the examples above and a filling bottle comprising a mouth, wherein the mouth may be configured to engage a surface of the sealing ring along a perimeter lying beyond an outermost extent of the cap.

In another example, a reservoir arranged and configured to couple to an endoscope for use in an endoscopic procedure may comprise a container configured to contain a fluid therein, the container extending from a first end to a second end and having a reduced diameter stem extending from the first end, the reduced diameter stem defining an opening for receiving a fluid, a water inlet, a gas inlet, and a port. The port may comprise a sealing ring defining an aperture extending from a first end to a second of the sealing ring, the aperture in fluid communication with the opening in the container, a cap positioned adjacent to the first end of the aperture of the sealing ring and configured to selectively form a fluid tight seal with the sealing ring, and a biasing mechanism disposed between the container and the sealing ring. The sealing ring may be movable between a first closed configuration and a second open configuration.

Alternatively or additionally to any of the examples above, in another example, when in the first closed configuration, the biasing mechanism may be configured to bias the sealing ring against the cap.

Alternatively or additionally to any of the examples above, in another example, when in the second open configuration, a force may be exerted on the first end of the sealing ring to move the sealing ring away from the cap.

Alternatively or additionally to any of the examples above, in another example, the reservoir may further comprise a tether extending between an interior of the container and the cap.

Alternatively or additionally to any of the examples above, in another example, the tether may comprise a first end coupled to the cap and a second end disposed within the interior of the container.

Alternatively or additionally to any of the examples above, in another example, the second end of the tether may be deformable between a first expanded configuration and a second collapsed configuration.

Alternatively or additionally to any of the examples above, in another example, when the second end of the tether is in the first expanded configuration, the second end of the of the tether may have a width greater than a width of the opening in the container.

Alternatively or additionally to any of the examples above, in another example, when the second end of the tether is in the second collapsed configuration, the second end of the of the tether may have a width less than a width of the opening in the container.

In another example, a reservoir arranged and configured to couple to an endoscope for use in an endoscopic procedure may comprise a container configured to contain a fluid therein, the container extending from a first end to a second end and having a reduced diameter stem extending from the first end, the reduced diameter stem defining an opening for receiving a fluid, a water inlet, a gas inlet, and a port disposed partially about the reduced diameter stem of the container. The port may comprise a sealing ring defining an aperture extending from a first end to a second of the sealing ring, the aperture in fluid communication with the opening in the container, an O-ring disposed between the sealing ring and the reduced diameter stem of the container, a cap positioned adjacent to the first end of the aperture of the sealing ring, and a biasing mechanism disposed between the first end of the container and the second end of the sealing ring, the biasing mechanism configured to bias the sealing ring into a sealed configuration with the cap. The sealing ring may be configured to move from the sealed configuration to an open configuration in response to a force exerted on the first end of the sealing ring.

These and other features and advantages of the present disclosure will be readily apparent from the following detailed description, the scope of the claimed invention being set out in the appended claims.

BRIEF DESCRIPTION OF THE DRAWINGS

The accompanying drawings, which are incorporated in and constitute a part of this specification, illustrate various exemplary embodiments and together with the description serve to explain the principles of the present disclosure.

Figure 1:
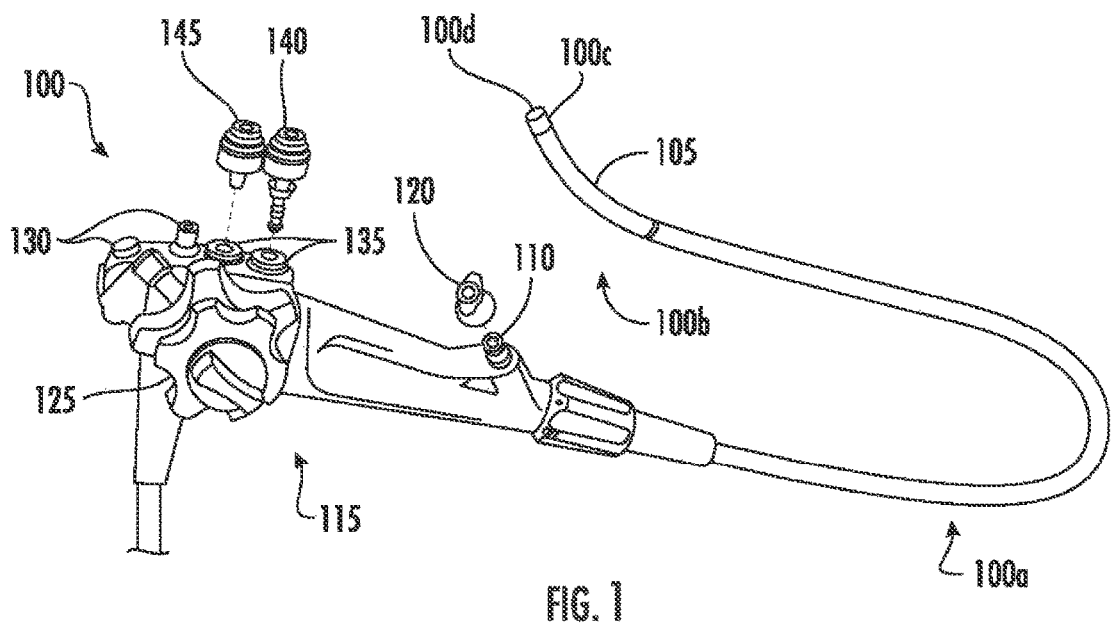
FIG. 1 depicts components of an endoscope.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

This disclosure is now described with reference to an exemplary medical system that may be used in endoscopic medical procedures. However, it should be noted that reference to this particular procedure is provided only for convenience and not intended to limit the disclosure. A person of ordinary skill in the art would recognize that the concepts underlying the disclosed devices and related methods of use may be utilized in any suitable procedure, medical or otherwise. This disclosure may be understood with reference to the following description and the appended drawings, the same or similar reference numbers will be used through the drawings to refer to the same or like parts.

The term "distal" refers to a portion farthest away from a user when introducing a device into a patient. By contrast, the term "proximal" refers to a portion closest to the user when placing the device into the patient. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." Further, as used herein, the terms "about," "approximately" and "substantially" indicate a range of values within +/−10% of a stated or implied value. Additionally, terms that indicate the geometric shape of a component/surface refer to exact and approximate shapes.

Embodiments of the present disclosure are described with specific reference to a bottle (e.g., container, reservoir, or the like) and tube assembly or set. It should be appreciated that such embodiments may be used to supply fluid and/or gas to an endoscope, for a variety of different purposes, including, for example to facilitate insufflation of a patient, lens washing, and/or to irrigate a working channel to aid in flushing/suctioning debris during an endoscopic procedure.

Although the present disclosure includes descriptions of a container and tube set suitable for use with an endoscope system to supply fluid and/or gas to an endoscope, the devices, systems, and methods herein could be implemented in other medical systems requiring fluid and/or gas delivery, and for various other purposes.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Conventionally, endoscope devices have been widely used for performing diagnostic and/or therapeutic treatments. During endoscopic procedures, physicians may use a combination of air, irrigation and lens wash as a means of flushing debris, cleaning optics, and insufflating the working lumen. To enable these capabilities compressed gasses from either the processor or alternative source are used to increase the pressure within a fluid bottle which either insufflates the working lumen or wash the lens of the endoscope. Additionally, a peristaltic pump can be used to irrigate the working lumen of debris. One of the challenges faced during endoscopic procedures is that the common water bottle and tube set used contain a maximum of 1 liter of water and are not designed to be refilled. This may force nurses/technicians to replace the water bottle multiple times a day. This may introduce multiple opportunities for contamination to the tube set by either contacting non-sterile surfaces or dropping the tubing on the floor. Disclosed herein are methods and systems to reduce or eliminate the need to disconnect the tube set and use a second bottle.

Figure 2:
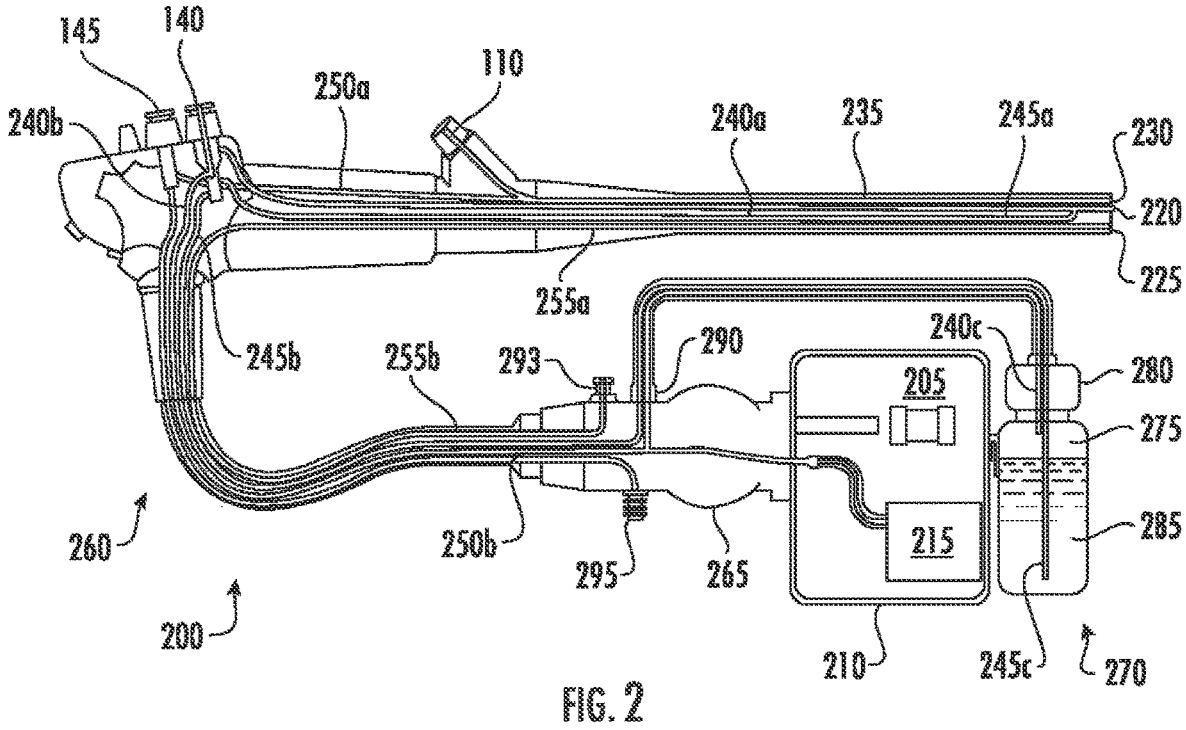
FIG. 2 depicts components of an endoscope system with endoscope, light source, light source connector, water reservoir, and tubing assembly for air and lens wash fluid delivery.

With reference to FIGS. 1-2, an exemplary endoscope 100 and system 200 are depicted that may comprise an elongated shaft 100a that is inserted into a patient. A light source 205 feeds illumination light to a distal portion 100b of the endoscope 100, which may house an imager (e.g., CCD or CMOS imager) (not shown). The light source 205 (e.g., lamp) is housed in a video processing unit 210 that processes signals that are input from the imager and outputs processed video signals to a video monitor (not shown) for viewing. The video processing unit 210 also serves as a component of an air/water feed circuit by housing a pressurizing pump 215, such as an air feed pump, in the unit.

The endoscope shaft 100a may include a distal tip 100c provided at the distal portion 100b of the shaft 100a and a flexible bending portion 105 proximal to the distal tip 100c. The flexible bending portion 105 may include an articulation joint (not shown) to assist with steering the distal tip 100c. On an end face 100d of the distal tip 100c of the endoscope 100 is a gas/lens wash nozzle 220 for supplying gas to insufflate the interior of the patient at the treatment area and for supplying water to wash a lens covering the imager. An irrigation opening 225 in the end face 100d supplies irrigation fluid to the treatment area of the patient. Illumination windows (not shown) that convey illumination light to the treatment area, and an opening 230 to a working channel 235 extending along the shaft 100a for passing tools to the treatment area, may also be included on the face 100d of the distal tip 100c. The working channel 235 extends along the shaft 100a to a proximal channel opening 110 positioned distal to an operating handle 115 of the endoscope 100. A biopsy valve 120 may be utilized to seal the channel opening 110 against unwanted fluid egress.

The operating handle 115 may be provided with knobs 125 for providing remote 4-way steering of the distal tip via wires connected to the articulation joint in the bendable flexible portion 105 (e.g., one knob controls up-down steering and another knob control for left-right steering). A plurality of video switches 130 for remotely operating the video processing unit 210 may be arranged on a proximal end side of the handle 115. In addition, the handle 115 is provided with dual valve wells 135. One of the valve wells 135 may receive a gas/water valve 140 for operating an insufflating gas and lens water feed operation. A gas supply line 240a and a lens wash supply line 245a run distally from the gas/water valve 140 along the shaft 100a and converge at the distal tip 100c proximal to the gas/wash nozzle 220 (FIG. 2). The other valve well 135 receives a suction valve 145 for operating a suction operation. A suction supply line 250a runs distally from the suction valve 145 along the shaft 100a to a junction point in fluid communication with the working channel 235 of the endoscope 100.

The operating handle 115 is electrically and fluidly connected to the video processing unit 210, via a flexible umbilical 260 and connector portion 265 extending therebetween. The flexible umbilical 260 has a gas (e.g., air or $CO_2$) feed line 240b, a lens wash feed line 245b, a suction feed line 250b, an irrigation feed line 255b, a light guide (not shown), and an electrical signal cable (not shown). The connector portion 265 when plugged into the video processing unit 210 connects the light source 205 in the video processing unit with the light guide. The light guide runs along the umbilical 260 and the length of the endoscope shaft 100a to transmit light to the distal tip 100c of the endoscope 100. The connector portion 265 when plugged into the video processing unit 210 also connects the air pump 215 to the gas feed line 240b in the umbilical 260.

A water reservoir or container 270 (e.g., water bottle) is fluidly connected to the endoscope 100 through the connector portion 265 and the umbilical 260. A length of gas supply tubing 240c passes from one end positioned in an air gap 275 between the top 280 (e.g., bottle cap) of the reservoir 270 and the remaining water 285 in the reservoir to a detachable gas/lens wash connection 290 on the outside of the connector portion 265. The detachable gas/lens wash connection 290 may be detachable from the connector portion 265 and/or the gas supply tubing 240c. The gas feed line 240b from the umbilical 260 branches in the connector portion 265 to fluidly communicate with the gas supply tubing 240c at the detachable gas/lens wash connection 290, as well as the air pump 215. A length of lens wash tubing 245c, with one end positioned at the bottom of the reservoir 270, passes through the top 280 of the reservoir 270 to the same detachable connection 290 as the gas supply tubing 240c on the connector portion 265. In other embodiments, the connections may be separate and/or separated from each other. The connector portion 265 also has a detachable irrigation connection 293 for irrigation supply tubing (not shown) running from a source of irrigation water (not shown) to the irrigation feed line 255b in the umbilical 260. The detachable irrigation connection 293 may be detachable from the connector portion 265 and/or the irrigation supply tubing (not shown). In some embodiments, irrigation water is supplied via a pump (e.g., peristaltic pump) from a water source independent (not shown) from the water reservoir 270. In other embodiments, the irrigation supply tubing and lens wash tubing 245c may source water from the same reservoir. The connector portion 265 may also include a detachable suction connection 295 for suction feed line 250b and suction supply line 250a fluidly connecting a vacuum source (e.g., hospital house suction) (not shown) to the umbilical 260 and endoscope 100. The detachable suction connection 295 may be detachable from the connector portion 265 and/or the suction feed line 250b and/or the vacuum source.

The gas feed line 240b and lens wash feed line 245b are fluidly connected to the valve well 135 for the gas/water valve 140 and configured such that operation of the gas/water valve in the well controls supply of gas or lens wash to the distal tip 100c of the endoscope 100. The suction feed line 250b is fluidly connected to the valve well 135 for the suction valve 145 and configured such that operation of the suction valve in the well controls suction applied to the working channel 235 of the endoscope 100.

Referring to FIG. 2, an exemplary operation of an endoscopic system 200, including an endoscope such as endoscope 100 above, is explained. Air from the air pump 215 in the video processing unit 210 is flowed through the connection portion 265 and branched to the gas/water valve 140 on the operating handle 115 through the gas feed line 240b in the umbilical 260, as well as through the gas supply tubing 240c to the water reservoir 270 via the connection 290 on the connector portion 265. When the gas/water valve 140 is in a neutral position, without the user's finger on the valve, air is allowed to flow out of the valve to atmosphere. In a first position, the user's finger is used to block the vent to atmosphere. Gas is allowed to flow from the valve 140 down the gas supply line 240a and out the distal tip 100c of the endoscope 100 in order to, for example, insufflate the treatment area of the patient. When the gas/water valve 140 is pressed downward to a second position, gas is blocked from exiting the valve, allowing pressure of the air passing from the air pump 215 to rise in the water reservoir 270. Pressurizing the water source forces water out of the lens wash tubing 245c, through the connector portion 265, umbilical 260, through the gas/water valve 140 and down the lens wash supply line 245a, converging with the gas supply line 240a prior to exiting the distal tip 100c of the endoscope 100 via the gas/lens wash nozzle 220. Air pump pressure may be calibrated to provide lens wash water at a relatively low flow rate compared to the supply of irrigation water.

The volume of the flow rate of the lens wash is governed by gas pressure in the water reservoir 270. When gas pressure begins to drop in the water reservoir 270, as water is pushed out of the reservoir 270 through the lens wash tubing 245c, the air pump 215 replaces lost air supply in the reservoir 270 to maintain a substantially constant pressure, which in turn provides for a substantially constant lens wash flow rate. In some embodiments, a filter (not shown) may be placed in the path of the gas supply tubing 240c to filter-out undesired contaminants or particulates from passing into the water reservoir 270. In some embodiments, outflow check valves or other one-way valve configurations (not shown) may be placed in the path of the lens wash supply tubing to help prevent water from back-flowing into the reservoir 270 after the water has passed the valve.

A relatively higher flow rate of irrigation water is typically required compared to lens wash, since a primary use is to clear the treatment area in the patient of debris that obstructs the user's field of view. Irrigation is typically achieved with the use of a pump (e.g., peristaltic pump), as described. In embodiments with an independent water source for irrigation, tubing placed in the bottom of a water source is passed through the top of the water source and threaded through the head on the upstream side of the pump. Tubing on the downstream side of the pump is connected to the irrigation feed line 255b in the umbilical 260 and the irrigation supply line 255a endoscope 100 via the irrigation connection 293 on the connector portion 265. When irrigation water is required, fluid is pumped from the water source by operating the irrigation pump, such as by depressing a footswitch (not shown), and flows through the irrigation connection 293, through the irrigation feed line 255b in the umbilical, and down the irrigation supply line in the shaft 100a of the endoscope to the distal tip 100c. In order to equalize the pressure in the water source as water is pumped out of the irrigation supply tubing, an air vent (not shown) may be included in the top 280 of the water reservoir 270. The vent allows atmospheric air into the water source preventing negative pressure build-up in the water source, which could create a vacuum that suctions undesired matter from the patient back through the endoscope toward the water source. In some embodiments, outflow check valves or other one-way valve configurations (not shown), similar to the lens wash tubing 245c, may be placed in the path of the irrigation supply tubing to help prevent back-flow into the reservoir after water has passed the valve.

FIGS. 3A-3D are schematic drawings illustrating the operation of an embodiment of a hybrid system 300 where the supply tubing for irrigation and lens wash are connected to and drawn from a single water reservoir. It is contemplated that fluids other than water may be used, such as, but not limited to saline. The hybrid system 300 includes the single water reservoir 305, a cap 310 for the reservoir, gas supply tubing 240c, lens wash supply tubing 245c, irrigation pump 315 with foot switch 318, upstream irrigation tubing 320 and downstream irrigation supply tubing 255c. The cap 310 may be configured to attach in a seal-tight manner to the water reservoir 305 by a typically threaded arrangement. The cap 310 may include a gasket to seal the cap 310 to the reservoir 305. The gasket can be an O-ring, flange, collar, and/or the like and can be formed of any suitable material. A number of through-openings (325a, 325b, 325c) in the cap 310 are provided to receive, respectively, the gas supply tubing 240c, lens wash supply tubing 245c, and upstream irrigation supply tubing 320. In FIGS. 3A-3D, the system depicted includes separate tubing for gas supply, lens wash, and irrigation.

In other embodiments, the gas supply tubing 240c and lens wash tubing 245c may be combined in a coaxial arrangement. Some illustrative coaxial arrangements are described in commonly assigned U.S. patent application Ser. No. 17/558,239, titled INTEGRATED CONTAINER AND TUBE SET FOR FLUID DELIVERY WITH AN ENDO-SCOPE and U.S. patent application Ser. No. 17/558,256, titled TUBING ASSEMBLIES AND METHODS FOR FLUID DELIVERY, the disclosures of which are hereby incorporated by reference. For example, the gas supply tubing may define a lumen that is sufficiently large in diameter to encompass a smaller diameter lens wash tubing, coaxially received within the gas supply tubing, as well as provide air to the water source in an annular space surrounding the lens wash tubing to pressurize the water reservoir (see, e.g., gas and lens wash supply tubing 240c, 245c). The lens wash supply tubing may be configured to exit the lumen defined by the coaxial gas supply tubing in any suitable sealed manner, such as, for example, an aperture, fitting, collar, and/or the like, for the purpose of transitioning from the coaxial arrangement to a side-by-side arrangement at the detachable gas/lens wash connection to the endoscope connector portion (e.g., connector portion 265 of FIG. 2).

In various embodiments, different configurations of valving (not shown) may be incorporated into various embodiments disclosed hereby, including the tubing of the systems 200, 300. For example, an in-flow check valve can be disposed in the path of the gas supply tubing 240c to help prevent backflow into the air pump 215. In this manner, pressure building within the water reservoir 305 creates a pressure difference between the water source and the gas supply tubing 240c helping to maintain a positive pressure in the water source even when large amounts of water may be removed from the water source during the irrigation function. This arrangement compensates for any time lag in air being delivered from the air pump 215 to the water reservoir 305, which might otherwise cause a negative pressure vacuum in the water reservoir. Similarly, an outflow check valve, such as the one-way valve with inlet/outlets and valve insert, may be incorporated in the lens wash supply tubing 240c, upstream irrigation supply tubing 320, and/or downstream irrigation supply tubing 255c to help prevent backflow of water from either or both of the lens wash and irrigation tubing in the event of a negative pressure situation, as described.

More generally, in many embodiments, a check valve may refer to any type of configuration for fluid to flow only in one direction in a passive manner. For example, a check valve may include, or refer to, one or more of a ball check valve, a diaphragm check valve, a swing check valve, a tilting disc check valve, a flapper valve, a stop-check valve, a lift-check valve, an in-line check valve, a duckbill valve, a pneumatic non-return valve, a reed valve, or a flow check. Accordingly, a check valve as used herein is meant to be separate and distinct from an active valve that is operated in a binary manner as an on/off valve or switch to allowed flow to be turned on or allow flow to be turned off (e.g., a stop cock valve, solenoid valve, peristaltic pump).

During operation of the system of FIGS. 3A-3D, a flow of water for irrigation may be achieved by operating the irrigation pump 315. A flow of water for lens wash may be achieved by depressing the gas/water valve 140 on the operating handle 115 of the endoscope 100. These functions may be performed independent of one another or simultaneously. When operating lens wash and irrigation at the same time, as fluid is removed from the water reservoir 305, the pressure in the system may be controlled to maintain the lens wash supply tubing 240c at substantially the pressure necessary to accomplish a lower flow rate lens wash, while compensating for reduced pressure in the water reservoir 305 due to supplying a high flow rate irrigation. When pressure is reduced in the water reservoir by use of the lens wash function, the irrigation function, or both functions simultaneously, the reduced pressure may be compensated for by the air pump 215 via the gas supply tubing 240c.

Figures 3A, 3B:
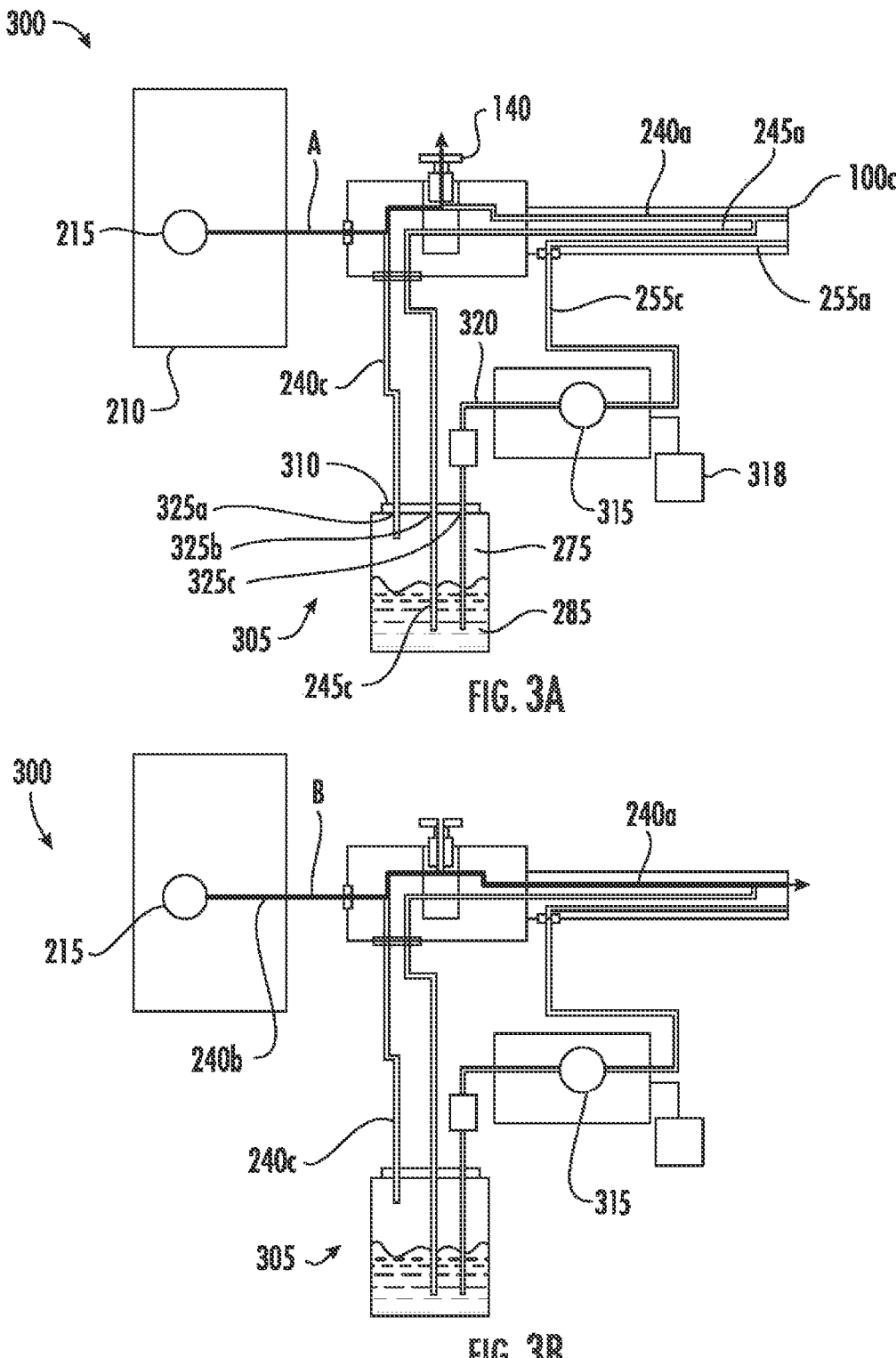
FIG. 3A depicts an endoscope system with endoscope, light source, water reservoir, and tubing assembly for hybrid air, lens wash and irrigation fluid delivery, wherein the system is activated to deliver air to atmosphere.
FIG. 3B depicts the endoscope system of FIG. 3A, wherein the system is activated to deliver air to a patient through the patient end of the endoscope.

The schematic set-up in FIGS. 3A-3D has been highlighted to show the different flow paths possible with the hybrid system 300 having supply tubing for irrigation 320 and lens wash 240c connected to and drawn from the single water reservoir 305. As shown in FIG. 3A, the endoscope 100 is in a neutral state with the gas/water valve 140 in an open position. The neutral state delivers neither gas, nor lens wash, to the distal tip of the endoscope. Rather gas (pressure) is delivered along path A from the pressurizing air pump 215 and vented through the gas feed line 240b in the umbilical 260 via the connector portion 265 and through the gas/water valve to atmosphere. Since the system is open at the vent hole in the gas/water valve 140, there is no build up to pressurize the water reservoir 305 and consequently no water is pushed through the lens wash supply tubing 240c.

As shown in FIG. 3B, the endoscope 100 is in a gas delivery state with the gas/water valve 140 in a first position. When gas is called for at the distal tip 100c, for example, to clean the end face 100d of the distal tip or insufflate the patient body in the treatment area, the user closes off the vent hole in the gas/water valve 140 with a thumb, finger, or the like (first position). In this state, gas (pressure) is delivered along path B from the air pump 215 and flowed through the gas feed line 240b in the umbilical 260 via the connector portion 265. The gas continues through the gas/water valve 140 to the gas supply line 240a in the endoscope shaft 100a and out the gas/lens wash nozzle 220 at the distal tip 100c. There is no build up to pressurize the water reservoir since the system is open at the gas/lens water nozzle 220, and consequently no water is pushed through the lens wash supply tubing 240c.

Figures 3C, 3D:
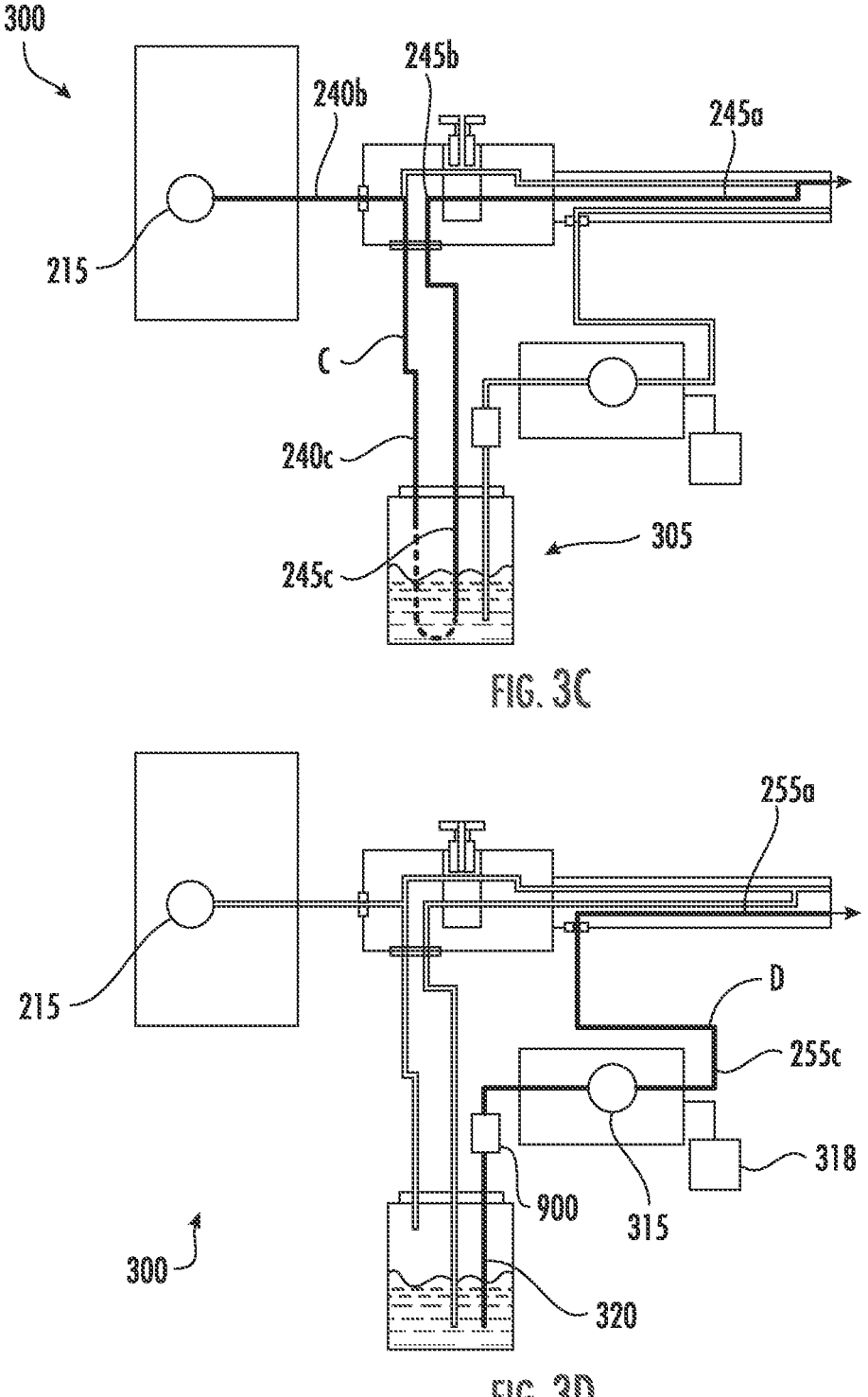
FIG. 3C depicts the endoscope system of FIG. 3A, wherein the system is activated to deliver lens wash fluid through the patient end of the endoscope.
FIG. 3D depicts the endoscope system of FIG. 3A, wherein the system is activated to deliver irrigation fluid through the patient end of the endoscope.

As shown in FIG. 3C, the endoscope 100 is in a lens wash delivery state with the gas/water valve 140 in a second position. When lens wash is called for at the distal tip 100c, for example, to clean the end face 100d of the distal tip 100c, the user, keeping the vent hole in the air/water valve closed off, depresses the valve 140 to its furthest point in the valve well 135. The second position blocks off the gas supply to both atmosphere and the gas supply line 240a in the endoscope, and opens up the gas/water valve 140 to allow lens wash water to pass through to the lens wash supply line 245a in the endoscope shaft 100a and out the gas/lens wash nozzle 220 at the distal tip 100c. In this state, gas (pressure) is delivered along path C from the air pump 215, through the branched line in the connector portion 265 and out of the gas supply tubing 240c to the water reservoir 305. The gas (pressure) pressurizes the surface of the remaining water 285 in the reservoir 305 and pushes water up the lens wash supply tube 245c to the connector portion 265. The pressurized lens wash water is pushed further through the lens wash feed line 245b in the umbilical 260 and through the gas/water valve 140. Since the system 300 is closed, gas pressure is allowed to build and maintain a calibrated pressure level in the water reservoir 305, rather than venting to atmosphere or being delivered to the patient. This pressure, along with the endoscope feed and supply lines and external tubing, translates to a certain range of flow rate of the lens wash.

As shown in FIG. 3D, the endoscope 100 is in an irrigation delivery state. This may be performed at the same or a different time from the delivery of gas and/or lens wash. When irrigation is called for at the distal tip 100c, for example, if visibility in the treatment area is poor or blocked by debris, or the like, the user activates the irrigation pump 315 (e.g., by depressing foot switch 318) to delivery water along path D. With the pump 315 activated, water is sucked out of the water reservoir 305 through the upstream irrigation supply tubing 320 and pumped along the downstream irrigation supply tubing 255c to the connector portion 265. The irrigation pump head pressure pushes the irrigation water further through the irrigation feed line 255b in the umbilical 260, through the irrigation supply line 255a in the endoscope shaft 100a, and out the irrigation opening 225 at the distal tip 100c without passing through the gas/water valve 140. The irrigation pump pressure may be calibrated, along with the endoscope irrigation feed and supply lines and external tubing, to deliver a certain range of flow rate of the irrigation fluid.

Figure 4:
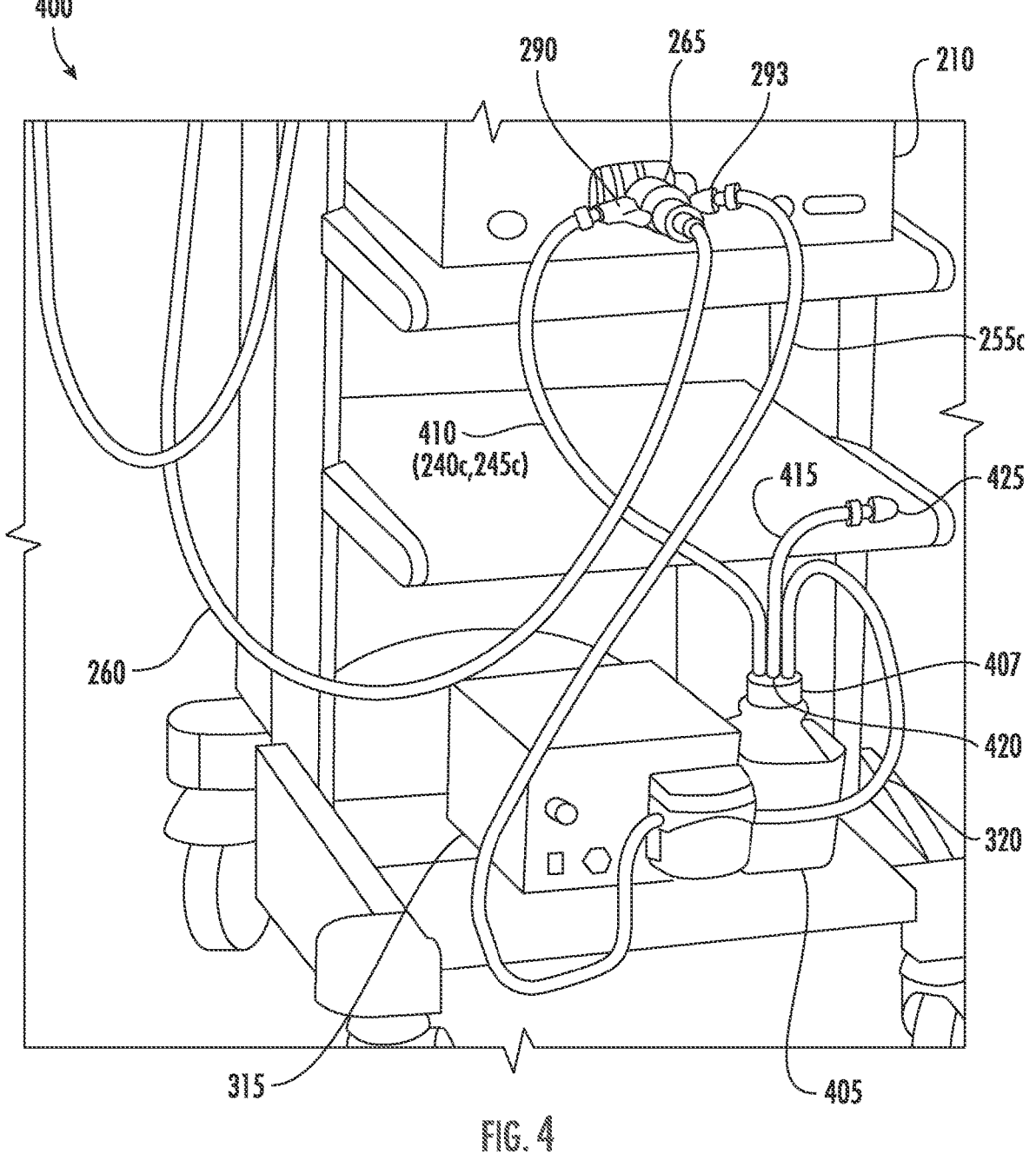
FIG. 4 depicts a hybrid endoscope system including a video processing unit, connector portion, peristaltic irrigation pump, water reservoir and top, coaxial gas and lens wash supply tubing, upstream and downstream irrigation supply tubing, and alternative gas supply tubing.

FIG. 4 is a schematic drawing illustrating a further embodiment of a hybrid system 400 including a video processing unit 210, connector portion 265, peristaltic irrigation pump 315, water reservoir 405 and top 407, coaxial gas and lens wash supply tubing 410, upstream and downstream irrigation supply tubing 320, 255c, respectively, and alternative gas (e.g., $CO_2$) supply tubing 415. A length of the alternative gas supply tubing 415 passes from one end positioned in the gas gap 275 (see FIG. 2) between the top 407 of the water reservoir 405 and the remaining water 285 in the reservoir through an additional opening 420 in the top of the reservoir to a detachable connection 425 for a source of the alternative gas supply (e.g., $CO_2$ hospital house gas source). When the alternative gas supply is desired, such as $CO_2$ gas, the air pump 215 on the video processing unit 210 may be turned off and $CO_2$ gas, rather than air, is thereby flowed to the water reservoir 405 pressurizing the water surface. Generally, the flow of $CO_2$ through the endoscope 100 is similar to the flow of air. In the neutral state, $CO_2$ gas flows backward up the gas supply tubing 240c to the connector portion 265, up the gas feed line 240b, and is vented through the gas/water valve 140 to atmosphere. In the first position, the user closes off the vent hole in the gas/water valve 140, and the $CO_2$ gas is flowed through the gas/water valve to the gas supply line 240a in the endoscope shaft 100a and out the gas/lens wash nozzle 220 at the distal tip 100c. In the second position, the user depresses the valve 140 to the bottom of the valve well 135, keeping the vent hole in the gas/water valve closed off. The second position blocks the $CO_2$ gas supply to both atmosphere and the gas supply line 240a in the endoscope 100, and opens up the gas/water valve 140 to allow lens wash water to pass through to the lens wash supply line 245a in the endoscope shaft 100a and out the gas/lens wash nozzle 220 at the distal tip 100c. Gas (pressure) in the reservoir 405 is maintained by delivery gas through alternative gas (e.g., $CO_2$) supply tubing 415. The irrigation function may be accomplished in a similar manner as the operation described above with respect to FIG. 3D.

Figure 5:
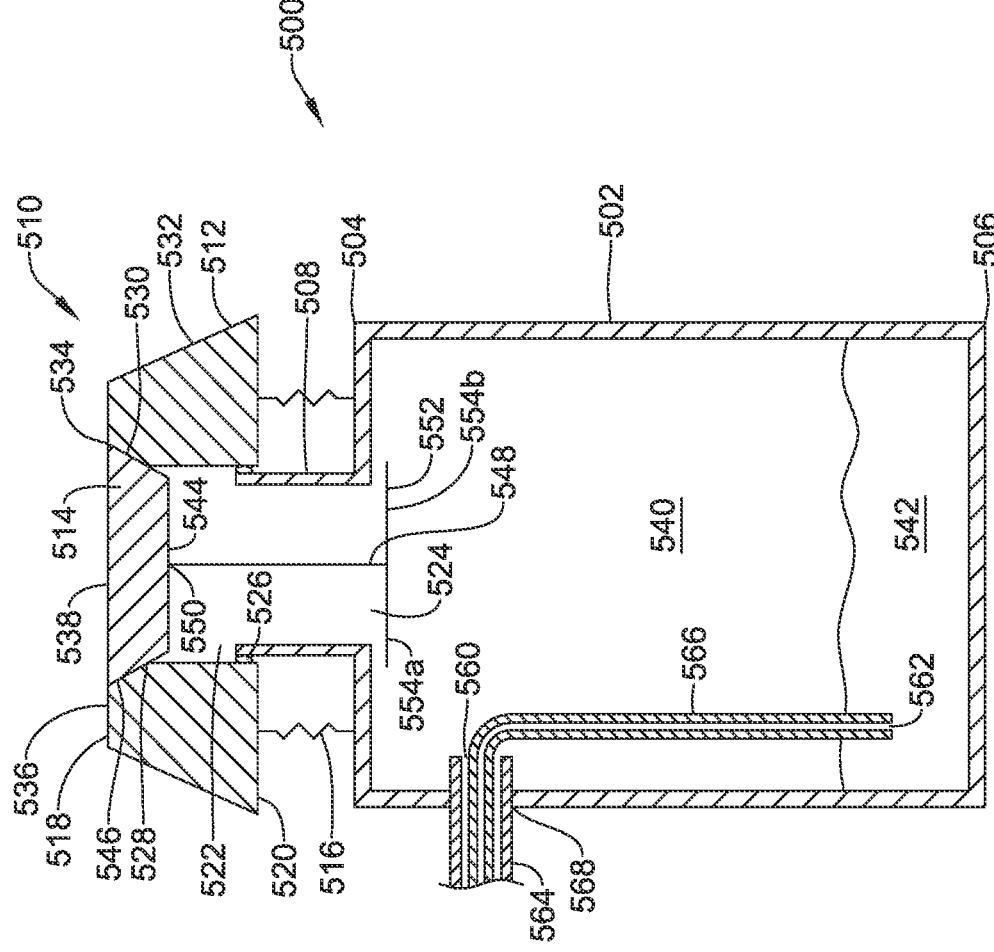
FIG. 5 depicts a cross-sectional view of an illustrative refillable reservoir in a first configuration.

As described above, it may be desirable to reduce opportunities for contamination to the tube set 240c, 245c, 320, 410, 415 during replacement of the water reservoir by providing a refillable water reservoir 270, 305, 405. FIG. 5 depicts a schematic cross-sectional view of an illustrative refillable fluid reservoir 500. The reservoir 500 may be configured to be used in an endoscopic system and includes components similar to the endoscope and endoscope systems described with regard to FIGS. 1-4; however, not all features may be described or shown here if not pertinent to the fluid circuit of the system. The reservoir 500 includes a container 502 configured to hold a fluid 542. In some embodiments, the container 502 may be configured to hold in the range of about 5 liters (L) to about 10 L of fluid. However, the container 502 may be configured to hold less than 5 L or more than 10 L if so desired.

The container 502 extends from a first or distal end 504 to a second or proximal end 506. A reduced diameter stem 508 may extend away from the first end 504 in a direction opposite the second end 506 of the container 502. Generally, the stem 508 may be a hollow cylindrical stem in fluid communication with an opening 524 of the container 502 and configured to selectively provide a fluid coupling between an exterior of the container 502 and an interior 540 of the container 502 to allow fluid 542 to be transferred into the container 502. The stem 508 may have a diameter, or cross-sectional dimension, that is less than a diameter, or cross-sectional dimension of the first or second ends 504, 506 of the container 502. In some cases, the container 502 and/or the stem 508 may have a generally cylindrical shape. However, this is not required. The container 502 and/or stem 508 may take any shape desired.

A port 510 may be disposed adjacent to stem 508 of the container 502. The port 510 in combination with the stem 508 may selectively fluidly couple a filling bottle or water bottle 570 (see, for example, FIG. 6) with the container 502 to allow fluid to pass from the filling bottle 570 to the interior 540 of the container 502. The port 510 may include a sealing ring 512, a cap 514, and a biasing mechanism 516. Each of the sealing ring 512, the cap 514, and the biasing mechanism 516 may be formed as separate components that are assembled together to form the port 510. Generally, the sealing ring 512 may be movable between a closed configuration (FIG. 5) for use of the reservoir 500 during an endoscopic procedure and an open configuration (FIG. 6) for refilling the reservoir 500. While the port 510 is illustrated as adjacent to the first end 504 or top of the container 502, the port 510 may be positioned at other locations on the container 502, as desired. In some embodiments, the port 510 may be at an end of a flexible attachment in fluid communication with the stem 508. It is contemplated that such an arrangement may allow the filling bottle 570 to be engaged with the port 510 prior to inverting the filling bottle 570 which may limit spillage when inverting the filling bottle 570.

Figure 6:
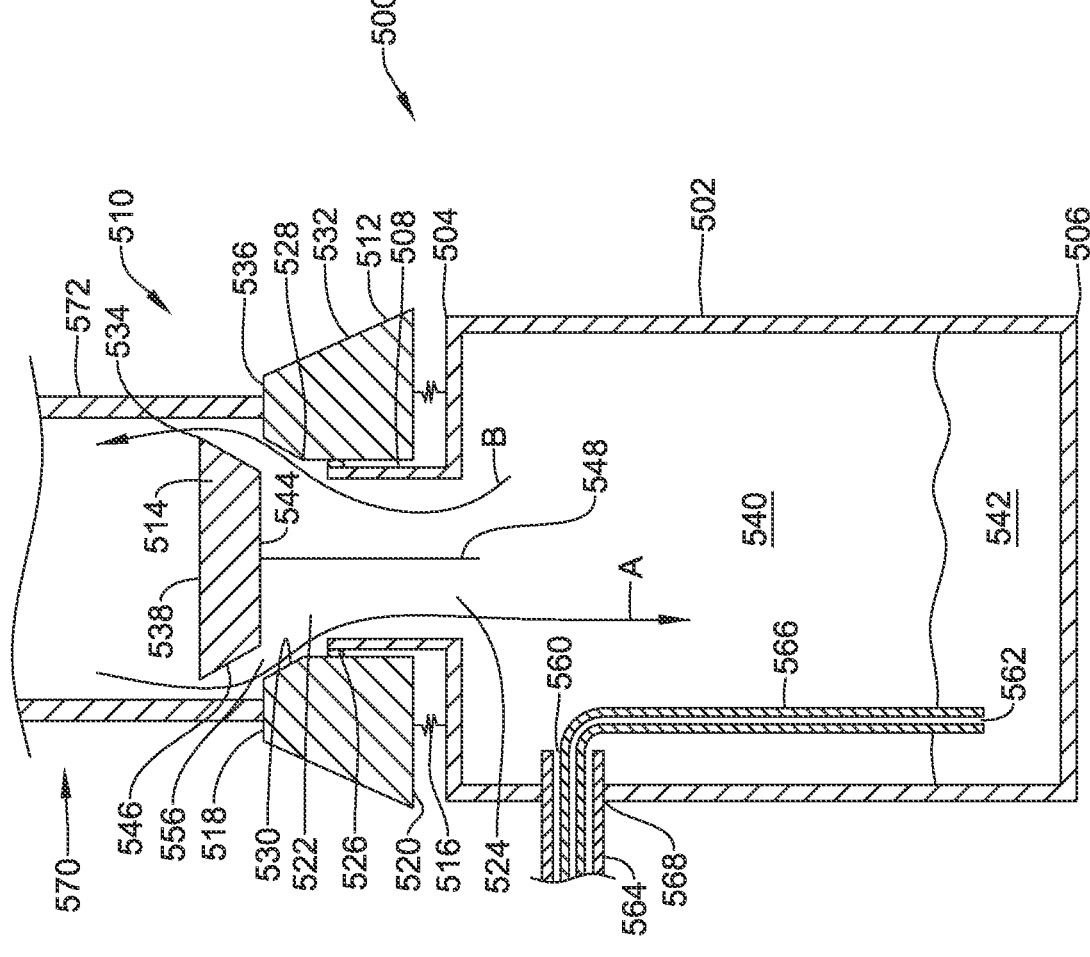
FIG. 6 depicts a cross-sectional view of the illustrative refillable reservoir of FIG. 5 in a second configuration.

The sealing ring 512 extends from a first or distal end 518 to a second or proximal end 520. An aperture 522 extends from the first end 518 to the second end 520 of the sealing ring 512. The aperture 522 may have a generally circular cross-section and have a diameter that is approximately the same as or larger than an outer diameter (or cross-sectional dimension) than the stem 508 such that the stem 508 may be received within the aperture 522. The aperture 522 may be disposed about at least a portion of an outer surface of the stem 508. In some embodiments, an O-ring 526 or other sealing member may be disposed between the inner wall of the aperture 522 and the outer surface of the stem 508. When so provided, the O-ring 526 may provide a fluid tight seal between the stem 508 and the port 510. This may allow the container 502 to be pressurized. The O-ring 526 may be positioned in a groove or recess formed in the outer surface of the stem 508 to maintain the O-ring 526 in a desired configuration as the sealing ring 512 is displaced, although this is not required. Alternatively, the O-ring 526 may be positioned in a groove or recess formed in the inner surface of the sealing ring 512 to maintain the O-ring 526 in a desired configuration as the sealing ring 512 is displaced, although this is not required. The O-ring 526 may be positioned such that it provides an air and liquid tight connection between the sealing ring 512 and the stem 508 when the sealing ring is in either the closed configuration (FIG. 5) or the open configuration (FIG. 6). In other embodiments, the inner wall of the aperture 522 may contact the outer surface of the stem 508 to form a fluid tight seal.

The diameter of the aperture 522 may decrease from a first diameter at the first end 518 to a second, smaller, diameter at an intermediate location 528 between the first and second ends 518, 520 to form a tapered first end region 530. The diameter of the aperture 522 may be substantially constant from the intermediate location 528 to the second end 520, although this is not required. It is contemplated that the diameter of the aperture 522 may take any configuration desired. For example, in some embodiments, the diameter may taper or decrease in size from the first end 518 to the second end 520. The tapered first end region 530 may be configured to mate with an outer diameter or outer surface of the cap 514, as will be described in more detail herein.

The sealing ring 512 extends radially outward from the aperture 522. The outer surface 532 of the sealing ring 512 may extend radially beyond the outermost extent 534 of the cap 514 such that a first end surface 536 is configured to engage a mouth of a filling bottle 570 (see, for example, FIG. 6). In some embodiments, the outer diameter of the sealing ring 512 may be tapered and increase from the first end 518 to the second end 520. It is contemplated that the tapered outer diameter may form an air and liquid tight connection with a range of filling bottle mouth diameters, for example, by insertion of the first end 518 of the sealing ring 512 into the filling bottle mouth such that the tapered outer diameter engages with the filling bottle mouth (not shown). However, this is not required. In some embodiments, the outer diameter of the sealing ring 512 may be substantially constant while in other embodiments, the outer diameter may decrease from the first end 518 to the second end 520.

The cap 514 may generally take the shape of a truncated cone. For example, the diameter of the cap 514 may decrease from a first diameter adjacent a first or distal end 538 to a second diameter adjacent a second or proximal end 544. The slope of the outer surface 546 of the cap 514 may generally conform to the slope of the tapered first end region 530 of the aperture 522 of the sealing ring 512 such that when the sealing ring 512 is biased towards the cap 514 a fluid tight seal is formed between the sealing ring 512 and the cap 514. The cap 514 may be held spaced distally away from the stem 508 by the biasing force of the biasing mechanism 516 and/or pressure within the interior 540 of the container 502. A tether 548 may extend between the second end 544 of the cap 514 and the interior 540 of the container 502. For example, a first end 550 of the tether 548 may be coupled to the second end 544 of the cap 514 and a second end 552 of the tether 548 may be positioned within the interior 540 of the container 502. The second end 552 of the tether 548 may include one or more radially extending elongate arms 554a, 554b (collectively, 554). The arms 554 may be deformable or movable between a first expanded configuration (shown in FIG. 5) and a second collapsed configuration. The arms 554 may have a thickness that is less than a diameter of opening 524 so that water and/or air may flow past the arms 554 and through the opening 524. For example, the arms 554 may have a generally rod-like shape, which may be of varying cross-section (e.g., circular, triangular, rectangular, or other polygonal cross-section). However, other shapes may be used, as desired.

In the expanded configuration, the arms 554 may extend at an angle to a longitudinal axis of the tether 548. In some embodiments, the arms 554 may extend generally orthogonal to the longitudinal axis of the tether 548 in a "tee" configuration, as shown in FIG. 5. However, this is not required. The arms 554 may extend at any angle relative to the longitudinal axis of the tether 548 which allows the second end 552 of the tether 548 to have a width greater that the diameter of the opening 524 of the container. In the collapsed configuration, the arms 554 may be biased towards the longitudinal axis of the tether 548 to reduce the outer profile thereof. This may allow the arms 554 to be inserted through the stem 508 and into the interior 540 of the container 502. The arms 554 may return to the expanded first configuration when the compressive force is released. In the expanded configuration, the arms 554 have a width that is greater than the inner diameter of the stem 508. Thus, once the second end 552 of the tether 548 is inserted into the interior 540 of the container 502, the arms 554 of the tether 548 resist removal of the cap 514 from the reservoir 500. For example, the arms 554 engage an inner surface of the container 502 to resist removal of the cap 514.

The biasing mechanism 516 may be positioned between the sealing ring 512 and the container 502. In some embodiments, the biasing mechanism 516 may be positioned between a second end 520 of the sealing ring 512 and a first end 504 of the container 502. The biasing mechanism 516 may be a mechanism configured to exert a distal force on the sealing ring 512. Some illustrative but non-limiting biasing mechanisms, may include, but are not limited to, coil springs, wave springs, compressible elastomers, shape memory rings or coils, bellows, hydraulic cylinders, etc. In some cases, the biasing mechanism 516 may be generally cylindrical and disposed about and radially spaced from the stem 508 of the container 502. The biasing mechanism 516 may be configured to compress in response to a proximal force exerted on the sealing ring 512 which in turn allows for proximal movement of the sealing ring 512, as will be described in more detail herein.

To assemble the port 510 with the container 502, the O-ring 526 may be installed onto the stem 508 of the container 502 (or with the sealing ring 512). The biasing mechanism 516 may then be placed around the stem 508. A second end of the biasing mechanism 516 may rest against the first end 504 of the container 502. The sealing ring 512 may then be placed around the stem 508. A second end 520 of the sealing ring 512 may be in contact with a first end of the biasing mechanism 516. The cap 514 may then be installed by inserting the second end 552 of the tether 548 through the stem 508 and into the interior 540 of the container 502. The second end 552 of the tether 548 engages the container 502 to prevent the cap 514 from uncoupling from the container. Further, the outer surface 546 of the cap 514 engages the tapered first end region 530 of the sealing ring 512 to secure the sealing ring 512 and biasing mechanism 516 to the container 502.

The reservoir 500 may include a gas inlet 560 and a water outlet 562 for coupling to a gas supply and a water supply tube. In some embodiments, the gas inlet 560 and/or water outlet 562 may be one or more ports for coupling separately provided gas supply lines and/or water supply lines. In other embodiments, the gas inlet 560 and/or water outlet 562 may be a part of a gas supply tubing 564 or water supply tubing 566. For example, reservoir 500 may be connected in fluid communication with a gas supply/alternate gas supply tubing (or gas supply tubing) 564 and a lens wash supply/irrigation supply tubing (or water supply tubing) 566. The gas supply tubing 564 extends from a second end external to the reservoir 500 through a reservoir opening 568 at or adjacent the first end 504 of the container 502. The shared gas supply tubing 564 may terminate within a reservoir gap, at or below the opening 568, but not extending into the remaining fluid 542 in the container 502 as shown. However, in some cases, the gas supply tubing 564 may extend into the fluid 542. For example, the opening 568 may be at a bottom or side of the container 502 such that the shared gas supply tubing 564 terminates within the fluid with gas bubbling up through the fluid 542 to pressurize the container 502. A lumen extends through the gas supply tubing 564 for receiving a flow of air and/or gas therethrough. The lumen of the gas supply tubing 564 is in operative fluid communication with an interior of the reservoir 500. The water supply tubing 566 extends from a second end external to the reservoir 500 through the reservoir opening 568, terminating in a first end within the remaining fluid 542 at or substantially at the bottom of the container 502. In some embodiments, the water supply tubing 566 may terminate at the opening 568. For example, when the opening 568 is at or adjacent to the second end 506 of the container 502, a dip tube may not be required. A lumen extends through the water supply tubing 566 for receiving a flow of fluid therethrough. The lumen of the lens wash supply/irrigation supply tubing 566 is in selective operative fluid communication with the bottom portion of the container 502. In the illustrated embodiment, the gas supply tubing 564 and the water supply tubing 566 may enter the container 502 through a single or common opening 568. For example, the gas supply tubing 564 and the water supply tubing 566 may be coaxially arranged as shown. However, this is not required. In some cases, the gas supply tubing 564 and the water supply tubing 566 may extend in a side by side arrangement or may be separately connected to the container 502 in different locations. The opening 568 may include a grommet, heat seal, or other sealing mechanism configured to seal the container 502 about the tubing 564, 566 in a fluid and pressure tight manner.

A portion of a gas supply tubing 564 and a portion of lens wash supply tubing 566 may extend from the reservoir 500, respectively, and may be connected in fluid communication with the endoscope at gas/lens wash connection on the connector portion 265 of the umbilical. The gas supply tubing 564 is connected in fluid communication with a gas pump (not explicitly shown) and/or gas feed line (not explicitly shown), and the lens wash supply tubing 566 is connected in fluid communication with lens wash feed line (not explicitly shown), within connector portion 265. While not explicitly shown, irrigation supply tubing may be coupled to the water supply tubing 566 via a manifold to supply irrigation fluid from the reservoir 500 or a separate irrigation supply tubing may be provided. For example, irrigation supply tubing (not shown) may extend from a second end external to the reservoir 500 through a reservoir opening (not shown), terminating in a first end within the remaining fluid 542 at or substantially at the bottom of the container 502.

Turning now to FIG. 6, it is contemplated that the reservoir 500 may be filled and refilled as needed by proximally displacing the sealing ring 512. The refilling of the reservoir 500 may be performed during a procedure or between procedures, as necessary. The water may be sterile or non-sterile, as desired. For example, sterile water may be used for therapeutic procedures while non-sterile water may be used for diagnostic procedures. As the external surfaces of the connection port 510 are non-sterile, prior to filling/refilling and subsequent contact with sterile water, the exterior may be wiped down with a disinfecting agent. It is contemplated that refilling the reservoir 500 with sterile or non-sterile water may create more flexibility and reduce the need to have as much sterile water in storage. Further, refilling the reservoir 500 via the port 510 may also remove the need to disconnect the reservoir 500 from the tubing 564, 566 throughout the day eliminating or greatly reducing the possibility of cross contamination by removing the need to replace the water container.

In FIG. 6, the second end 552 of the tether 548 is not illustrated to more clearly show the flow of water and air between the filling bottle 570 and the container 502. However, it should be understood that the second end 552 of the tether 548 remains within the container 502 during filling of the container 502. To fill the container 502, a mouth 572 of a filling bottle 570 is placed on or over the sealing ring 512. In the illustrated embodiment, the mouth 572 of the filling bottle 570 is placed against the first end surface 536 of the sealing ring 512. However, in some cases, the mouth 572 of the filling bottle 570 may be placed against the tapered outer surface 532 of the sealing ring 512. A proximal force is exerted on the filling bottle 570 which compresses the biasing mechanism 516 and allows the sealing ring 512 to move proximally towards the container. As the container 502 is pressurized during use, the positive pressure within the interior of the container 502 maintains the cap 514 in a fixed relationship to the container 502. Said differently, as the sealing ring 512 moves proximally, the cap 514 remains relatively fixed to define a gap 556 between the outer surface 546 of the cap 514 and the tapered first end region 530. The gap 556 allows water to flow down into the container 502 along flow path A while air moves up into the filling bottle 570 along flow path B. As the flow of water continues into the container 502, buoyant forces maintain the cap 514 in a spaced configuration from the sealing ring 512. When the filling bottle 570 is empty and/or when the container 502 is filled to the desired amount, the proximal force on the filling bottle 570 may be removed. This removes the proximal force on the biasing mechanism 516 and the biasing mechanism 516 presses the sealing ring 512 distally until the sealing ring 512 engages with the cap 514, as shown in FIG. 5. In some cases, more than one filling bottle 570 may be used to fill the container 502.

Figure 7:
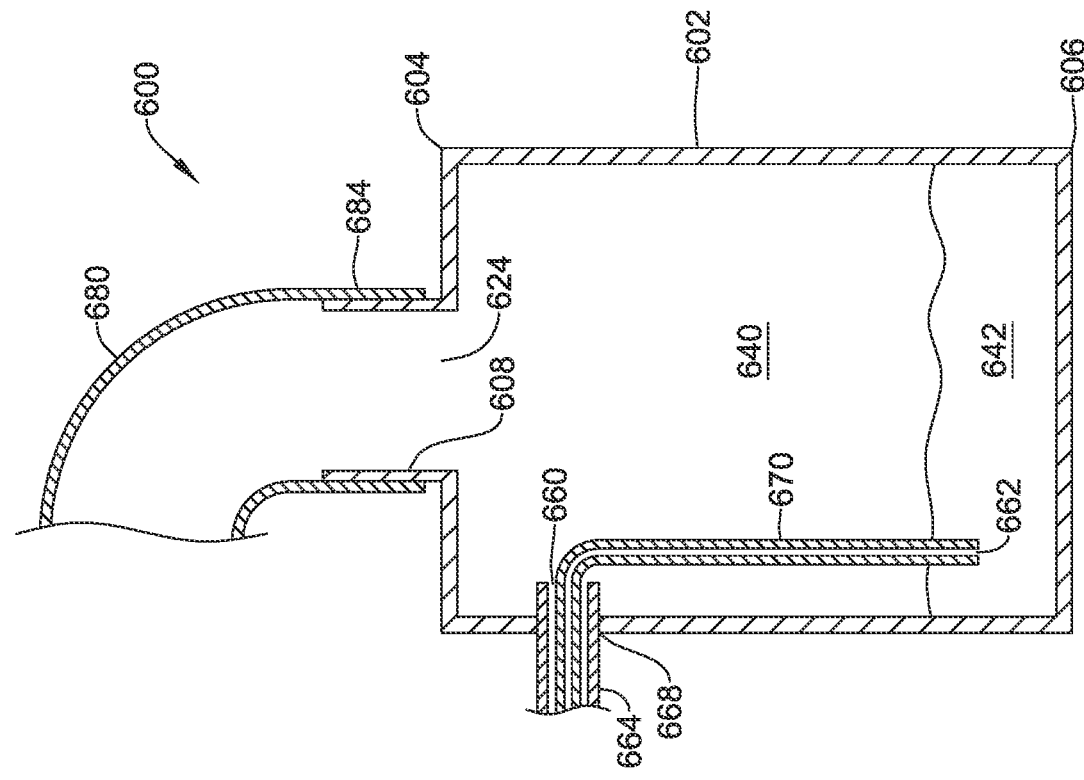
FIG. 7 depicts a cross-sectional view of another illustrative refillable reservoir in a first configuration.
Figure 7:
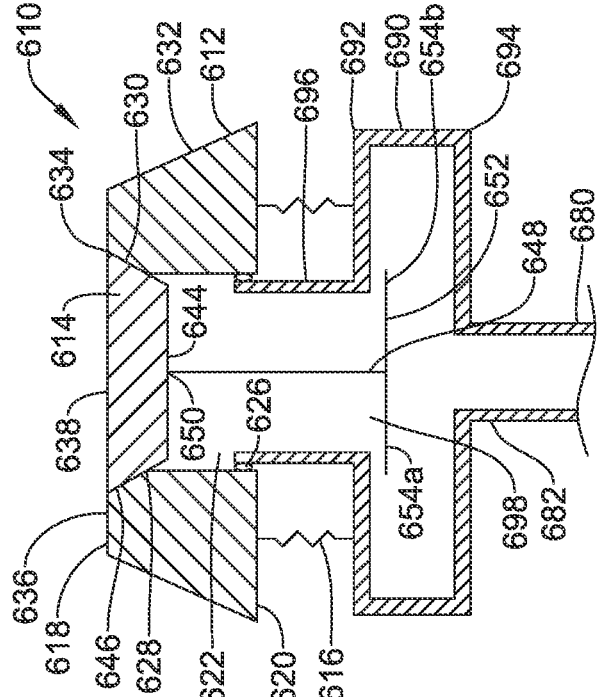

FIG. 7 depicts a schematic cross-sectional view of another illustrative refillable fluid reservoir 600. The reservoir 600 may be configured to be used in an endoscopic system and includes components similar to the endoscope and endoscope systems described with regard to FIGS. 1-4; however, not all features may be described or shown here if not pertinent to the fluid circuit of the system. The reservoir 600 includes a container 602 configured to hold a fluid 642. In some embodiments, the container 602 may be configured to hold in the range of about 5 liters (L) to about 10 L of fluid. However, the container 602 may be configured to hold less than 5 L or more than 10 L if so desired.

The container 602 extends from a first or distal end 604 to a second or proximal end 606. A reduced diameter stem 608 may extend distally away from the first end 604 in a direction opposite the second end 606 of the container 602. Generally, the stem 608 may be a hollow cylindrical stem in fluid communication with an opening 624 of the container 602 and configured to selectively provide a fluid coupling between an exterior of the container 602 and an interior 640 of the container 602 to allow fluid 642 to be transferred into the container 602. In some embodiments, the stem 608 may have a diameter, or cross-sectional dimension, that is less than a diameter, or cross-sectional dimension of the first or second ends 604, 606 of the container 602, although this is not required. In some cases, the container 602 and/or the stem 608 may have a generally cylindrical shape. However, this is not required. The container 602 and/or stem 608 may take any shape desired.

A port 610 may be connected to the stem 608 of the container 602 via a flexible tubing line 680. For example, a first end 682 of the flexible tubing line 680 may be fluidly coupled to the port 610 while a second end 684 of the line 680 is fluidly coupled to the container 602 through the stem 608. In some instances, the stem 608 may be omitted and the flexible tubing line 680 directly coupled to the opening 624 or other port in the container 602. The flexible tubing line 680 may be a separate component from the container 602 and/or port 610 or may be formed as a unitary structure with the container 602 and/or port 610. The port 610 in combination with the stem 608 may selectively fluidly couple a filling bottle or water bottle with the container 602 to allow fluid to pass from the filling bottle to the interior 640 of the container 602. The port 610 may include a sealing ring 612, a cap 614, a biasing mechanism 616, and a housing 690. Each of the sealing ring 612, the cap 614, the biasing mechanism 616, and the housing 690 may be formed as separate components that are assembled together to form the port 610. Generally, the sealing ring 612 may be movable between a closed configuration (FIG. 7) for use of the reservoir 600 during an endoscopic procedure and an open configuration (not explicitly shown) for refilling the reservoir 600. It is contemplated that the sealing ring 612 may function in a manner similar to that described with respect to FIG. 6. It is contemplated that spacing the port 610 from the container 602 may allow the filling bottle to be engaged with the port 610 prior to inverting the filling bottle which may limit or eliminate spillage when inverting the filling bottle.

The housing 690 extends from a first or distal end 692 to a second or proximal end 694. A reduced diameter housing stem 696 may extend distally away from the first end 692 in a direction opposite the second end 694 of the housing 690. Generally, the housing stem 696 may be a hollow cylindrical stem in fluid communication with the interior of the housing 690 via an opening 698 and the flexible tubing line 680 to selectively provide a fluid coupling between an exterior of the container 602 and an interior 640 of the container 602 to allow fluid 642 to be transferred into the container 602. In some embodiments, the housing stem 696 may have a diameter, or cross-sectional dimension, that is less than a diameter, or cross-sectional dimension of the first or second ends 692, 694 of the housing 690, although this is not required. In some cases, the housing 690 and/or the housing stem 696 may have a generally cylindrical shape. However, this is not required. The housing 690 and/or the housing stem 696 may take any shape desired.

The sealing ring 612 extends from a first or distal end 618 to a second or proximal end 620. An aperture 622 extends from the first end 618 to the second end 620 of the sealing ring 612. The aperture 622 may have a generally circular cross-section and have a diameter that is approximately the same as or larger than an outer diameter (or cross-sectional dimension) than the housing stem 696 such that the housing stem 696 may be received within the aperture 622. The aperture 622 may be disposed about at least a portion of an outer surface of the housing stem 696. In some embodiments, an O-ring 626 or other sealing member may be disposed between the inner wall of the aperture 622 and the outer surface of the housing stem 696. When so provided, the O-ring 626 may provide a fluid tight seal between the housing stem 696 and the port 610. This may allow the container 602 to be pressurized. The O-ring 626 may be positioned in a groove or recess formed in the outer surface of the housing stem 696 to maintain the O-ring 626 in a desired configuration as the sealing ring 612 is displaced, although this is not required. Alternatively, the O-ring 626 may be positioned in a groove or recess formed in the inner surface of the sealing ring 612 to maintain the O-ring 626 in a desired configuration as the sealing ring 612 is displaced, although this is not required. The O-ring 626 may be positioned such that it provides an air and liquid tight connection between the sealing ring 612 and the housing stem 696 when the sealing ring is in either the closed configuration (FIG. 7) or the open configuration (not explicitly shown). In other embodiments, the inner wall of the aperture 622 may contact the outer surface of the housing stem 696 to form a fluid tight seal.

The diameter of the aperture 622 may decrease from a first diameter at the first end 618 to a second, smaller, diameter at an intermediate location 628 between the first and second ends 618, 620 to form a tapered first end region 630. The diameter of the aperture 622 may be substantially constant from the intermediate location 628 to the second end 620, although this is not required. It is contemplated that the diameter of the aperture 622 may take any configuration desired. For example, in some embodiments, the diameter may taper or decrease in size from the first end 618 to the second end 620. The tapered first end region 630 may be configured to mate with an outer diameter or outer surface of the cap 614, as will be described in more detail herein.

The sealing ring 612 extends radially outward from the aperture 622. The outer surface 632 of the sealing ring 612 may extend radially beyond the outermost extent 634 of the cap 614 such that a first end surface 636 is configured to engage a mouth of a filling bottle. In some embodiments, the outer diameter of the sealing ring 612 may be tapered and increase from the first end 618 to the second end 620. It is contemplated that the tapered outer diameter may form an air and liquid tight connection with a range of filling bottle mouth diameters, for example, by insertion of the first end 618 of the sealing ring 612 into the filling bottle mouth such that the tapered outer diameter engages with the filling bottle mouth (not shown). However, this is not required. In some embodiments, the outer diameter of the sealing ring 612 may be substantially constant while in other embodiments, the outer diameter may decrease from the first end 618 to the second end 620.

The cap 614 may generally take the shape of a truncated cone. For example, the diameter of the cap 614 may decrease from a first diameter adjacent a first or distal end 638 to a second diameter adjacent a second or proximal end 644. The slope of the outer surface 646 of the cap 614 may generally conform to the slope of the tapered first end region 630 of the aperture 622 of the sealing ring 612 such that when the sealing ring 612 is biased towards the cap 614 a fluid tight seal is formed between the sealing ring 612 and the cap 614. The cap 614 may be held spaced distally away from the housing stem 696 by the biasing force of the biasing mechanism 616 and/or pressure within the interior 640 of the container 602. A tether 648 may extend between the second end 644 of the cap 614 and the interior of the housing 690. For example, a first end 650 of the tether 648 may be coupled to the second end 644 of the cap 614 and a second end 652 of the tether 648 may be positioned within the interior of the housing 690. The second end 652 of the tether 648 may include one or more radially extending elongate arms 654a, 654b (collectively, 654). The arms 654 may be deformable or movable between a first expanded configuration (shown in FIG. 7) and a second collapsed configuration (not explicitly shown). The arms 654 may have a thickness that is less than a diameter of an opening 698 of the housing 690 so that water and/or air may flow past the arms 654 and through the opening 698. For example, the arms 654 may have a generally rod-like shape, which may be of varying cross-section (e.g., circular, triangular, rectangular, or other polygonal cross-section). However, other shapes may be used, as desired.

In the expanded configuration, the arms 654 may extend at an angle to a longitudinal axis of the tether 648. In some embodiments, the arms 654 may extend generally orthogonal to the longitudinal axis of the tether 648 in a "tee" configuration, as shown in FIG. 7. However, this is not required. The arms 654 may extend at any angle relative to the longitudinal axis of the tether 648 which allows the second end 652 of the tether 648 to have a width greater that the diameter of the opening 698 of the housing 690. In the collapsed configuration, the arms 654 may be biased towards the longitudinal axis of the tether 648 to reduce the outer profile thereof. This may allow the arms 654 to be inserted through the housing stem 696 and into the interior of the housing 690. The arms 654 may return to the expanded first configuration when the compressive force is released. In the expanded configuration, the arms 654 have a width that is greater than the inner diameter of the housing stem 696. Thus, once the second end 652 of the tether 648 is inserted into the interior of the housing 690, the arms 654 of the tether 648 resist removal of the cap 614 from housing 690. For example, the arms 654 engage an inner surface of the housing 690 to resist removal of the cap 614.

The biasing mechanism 616 may be positioned between the sealing ring 612 and the housing 690. In some embodiments, the biasing mechanism 616 may be positioned between a second end 620 of the sealing ring 612 and a first end 692 of the housing 690. The biasing mechanism 616 may be a spring or other mechanism configured to exert a distal force on the sealing ring 612. In some cases, the biasing mechanism 616 may be generally cylindrical and disposed about and radially spaced from the housing stem 696 of the housing 690. The biasing mechanism 616 may be configured to compress in response to a proximal force exerted on the sealing ring 612 which in turn allows for proximal movement of the sealing ring 612, as will be described in more detail herein.

To assemble the port 610 with the housing 690, the O-ring 626 may be installed onto the housing stem 696 of the housing 690 (or with the sealing ring 612). The biasing mechanism 616 may then be placed around the housing stem 696. A second end of the biasing mechanism 616 may rest against the first end 692 of the housing 690. The sealing ring 612 may then be placed around the housing stem 696. A second end 620 of the sealing ring 612 may be in contact with a first end of the biasing mechanism 616. The cap 614 may then be installed by inserting the second end 652 of the tether 648 through the housing stem 696 and into the interior of the housing 690. The second end 652 of the tether 648 engages the housing 690 and prevents the cap 614 from uncoupling from the container. Further, the outer surface 646 of the cap 614 engages the tapered first end region 630 of the sealing ring 612 to secure the sealing ring 612 and biasing mechanism 616 to the housing 690.

The reservoir 600 may include a gas inlet 660 and a water outlet 662 for coupling to a gas supply and a water supply tube. In some embodiments, the gas inlet 660 and/or water outlet 662 may be one or more ports for coupling separately provided gas supply lines and/or water supply lines. In other embodiments, the gas inlet 660 and/or water outlet 662 may be a part of a gas supply tubing 664 or water supply tubing 670. For example, the reservoir 600 may be connected in fluid communication with a gas supply/alternate gas supply tubing (or gas supply tubing) 664 and a lens wash supply/irrigation supply tubing (or water supply tubing) 670. The gas supply tubing 664 extends from a second end external to the reservoir 600 through a reservoir opening 668 at or adjacent the first end 604 of the container 602. The shared gas supply tubing 664 may terminate within a reservoir gap, at or below the opening 668, but not extending into the remaining fluid 642 in the container 602, as shown. However, in some cases, the gas supply tubing 664 may extend into the fluid 642. For example, the opening 668 may be at a bottom or side of the container 602 such that the shared gas supply tubing 664 terminates within the fluid with gas bubbling up through the fluid 642 to pressurize the container 602. A lumen extends through the gas supply tubing 664 for receiving a flow of air and/or gas therethrough. The lumen of the gas supply tubing 664 is in operative fluid communication with an interior of the reservoir 600. The water supply tubing 670 extends from a second end external to the reservoir 600 through the reservoir opening 668, terminating in a first end within the remaining fluid 642 at or substantially at the bottom of the container 602. In some embodiments, the water supply tubing 670 may terminate at the opening 668. For example, when the opening 668 is at or adjacent to the second end 606 of the container 602 a dip tube may not be required. A lumen extends through the water supply tubing 670 for receiving a flow of fluid therethrough. The lumen of the lens wash supply/irrigation supply tubing 670 is in selective operative fluid communication with the bottom portion of the container 602. In the illustrated embodiment, the gas supply tubing 664 and the water supply tubing 670 may enter the container 602 through a single or common opening 668. For example, the gas supply tubing 664 and the water supply tubing 670 may be coaxially arranged, as shown. However, this is not required. In some cases, the gas supply tubing 664 and the water supply tubing 670 may extend in a side by side arrangement or may be separately connected to the container 602 in different locations. The opening 668 may include a grommet, heat seal, or other sealing mechanism configured to seal the container 602 about the tubing 664, 670 in a fluid and pressure tight manner.

A portion of a gas supply tubing 664 and a portion of lens wash supply tubing 670 may extend from the reservoir 600, respectively, and may be connected in fluid communication with the endoscope at gas/lens wash connection on the connector portion 265 of the umbilical. The gas supply tubing 664 is connected in fluid communication with a gas pump (not explicitly shown) and gas feed line (not explicitly shown), and the lens wash supply tubing 670 is connected in fluid communication with lens wash feed line (not explicitly shown), within connector portion 265. While not explicitly shown, irrigation supply tubing may be coupled to the water supply tubing 670 via a manifold to supply irrigation fluid from the reservoir 600 or a separate irrigation supply tubing may be provided. For example, irrigation supply tubing (not shown) may extend from a second end external to the reservoir 600 through a reservoir opening (not shown), terminating in a first end within the remaining fluid 642 at or substantially at the bottom of the container 602.

It is contemplated that the reservoir 600 may be filled and refilled as needed by proximally displacing the sealing ring 612. The reservoir 600 may be filled/refilled in a similar manner to the reservoir 500 described above. The refilling of the reservoir 600 may be performed during a procedure or between procedures, as necessary. The water may be sterile or non-sterile, as desired. For example, sterile water may be used for therapeutic procedures while non-sterile water may be used for diagnostic procedures. As the external surfaces of the connection port 610 are non-sterile, prior to filling/refilling and subsequent contact with sterile water, the exterior may be wiped down with a disinfecting agent. It is contemplated that refilling the reservoir 600 with sterile or non-sterile water may create more flexibility and reduce the need to have as much sterile water in storage. Further, refilling the reservoir 600 via the port 610 may also remove the need to disconnect the reservoir 600 from the tubing 664, 670 throughout the day eliminating or greatly reducing the possibility of cross contamination by removing the need to replace the water container.

To fill the container 602, a mouth of a filling bottle is placed on or over the sealing ring 612. The mouth of the filling bottle may be placed against the first end surface 636 of the sealing ring 612 or against the tapered outer surface 632 of the sealing ring 612 depending on a size of the mouth. It is contemplated that the flexible tubing line 680 may allow the filling bottle to remain upright until the mouth is engaged with the sealing ring 612. This may prevent or limit spills from the filling bottle during inversion thereof. Once engaged with the sealing ring 612, the filling bottle may be inverted and a proximal force exerted on the filling bottle which compresses the biasing mechanism 616 and allows the sealing ring 612 to move proximally towards the housing 690. As the container 602 is pressurized during use, the positive pressure within the interior of the container 602 extends through the flexible tubing line 680 to maintain the cap 614 in a fixed relationship to the housing 690. Said differently, as the sealing ring 612 moves proximally, the cap 614 remains relatively fixed to define a gap between the outer surface 646 of the cap 614 and the tapered first end region 630. The gap allows water to flow down into the container 602 along through the flexible tubing line 680 while air moves up into the filling bottle through the flexible tubing line 680. As the flow of water continues into the container 602, buoyant forces maintain the cap 614 in spaced configuration from the sealing ring 612. When the filling bottle is empty and/or when the container 602 is filled to the desired amount, the proximal force on the filling bottle may be removed. This removes the proximal force on the biasing mechanism 616 and the biasing mechanism 616 presses the sealing ring 612 distally until the sealing ring 612 engages with the cap 614, as shown in FIG. 7. In some cases, more than one filling bottle may be used to fill the container 602.

Figure 8:
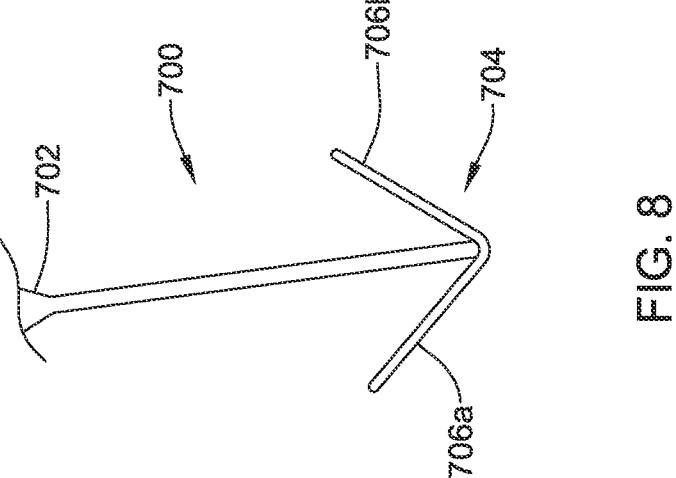
FIG. 8 is a side view of an alternative illustrative tether.

FIG. 8 depicts a side view of a portion of another illustrative tether 700. The tether 700 may be configured to extend between a cap 514, 614 and the container 502 and/or housing 690. For example, a first end 702 of the tether 700 may be coupled to the cap 514, 614 and a second end 704 of the tether 700 may be positioned within the interior of the container 502 and/or housing 690. The second end 704 of the tether 700 may include one or more radially extending elongate arms 706a, 706b (collectively, 706). The arms 706 may be deformable or movable between a first expanded configuration (shown in FIG. 8) and a second collapsed configuration (not explicitly shown). The arms 706 may have a thickness that is less than a diameter of an opening 524, 698 of the container 502 or housing 690 so that water and/or air may flow past the arms 706 and through the opening 524, 698. For example, the arms 706 may have a generally rod-like shape. However, other shapes may be used, as desired.

In the expanded configuration, the arms 706 may extend at an angle to a longitudinal axis of the tether 700. In some embodiments, the arms 706 may extend at an angle with the free ends thereof pointed towards the first end 702 of the tether 700 in an arrow or "vee" configuration, as shown in FIG. 7. However, this is not required. The arms 706 may extend at any angle relative to the longitudinal axis of the tether 700 which allows the second end 704 of the tether 700 to have a width greater that the diameter of the opening 524, 698 of the container 502 or housing 690. In the collapsed configuration, the arms 706 may be biased towards the longitudinal axis of the tether 700 to reduce the outer profile thereof. This may allow the arms 706 to be inserted through the housing stem 696 and into the interior of the housing 690 or through the stem 508 and into the interior 540 of the container 502. The arms 706 may return to the expanded first configuration when the compressive force is released. In the expanded configuration, the arms 706 have a width that is greater than the inner diameter of the stem 508 or the housing stem 696. Thus, once the second end 704 of the tether 700 is inserted into the interior of the housing 690, the arms 706 of the tether 700 resist removal of the cap 514, 614 from the container 502 or housing 690. For example, the arms 706 engage an inner surface of the container 502 or the housing 690 to resist removal of the cap 514, 614.

Figure 9:
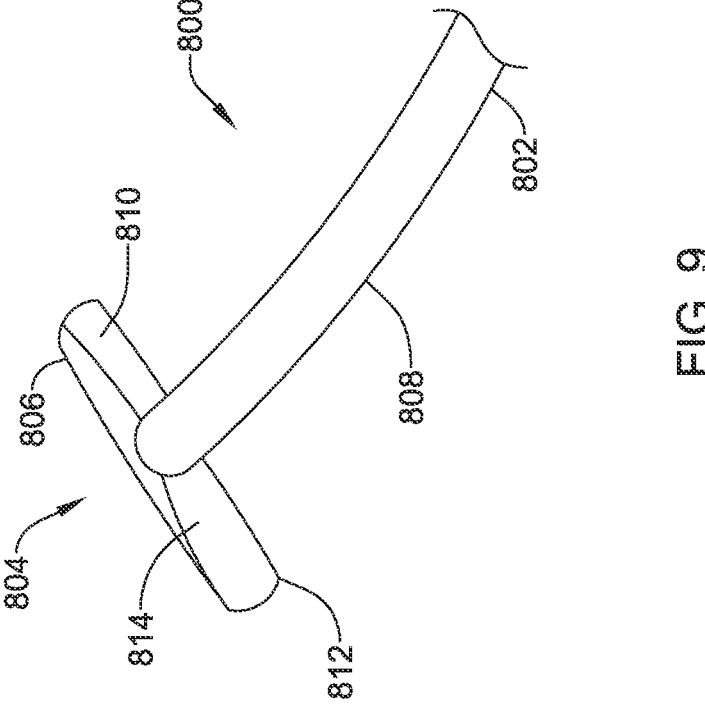
FIG. 9 is a perspective view of another illustrative tether.

FIG. 9 depicts a perspective view of a portion of another illustrative tether 800. The tether 800 may be configured to extend between a cap 514, 614 and the container 502 and/or housing 690. For example, a first end 802 of the tether 800 may be coupled to the cap 514, 614 and a second end 804 of the tether 800 may be positioned within the interior of the container 502 and/or housing 690. The second end 804 of the tether 800 may include an aglet 806 configured to be secured to an intermediate portion 808. The aglet 806 may be a sheath configured to surround a portion of the intermediate portion 808. In some cases, the aglet 808 may be made from a more rigid material than the intermediate portion 808, although this is not required. The aglet 806 may include a generally enclosed connecting portion 810 and a free end 812. The connecting portion 810 may be coupled to the intermediate portion 808 while the free end 812 is not. The free end 812 may move between a first expanded configuration (shown in FIG. 8) and a second collapsed configuration (not explicitly shown). In some cases, the free end 812 may define a cavity 814 configured to receive the intermediate portion 808 when the aglet 806 is in the collapsed configuration. The aglet 806 may have a thickness that is less than a diameter of an opening 524, 698 of the container 502 or housing 690 so that water and/or air may flow past the aglet 806 and through the opening 524, 698.

In the expanded configuration, the aglet 806 may extend at an angle to a longitudinal axis of the tether 800. In some embodiments, the aglet 806 may extend generally orthogonal to the intermediate portion 808. However, this is not required. The aglet 806 may extend at any angle relative to the longitudinal axis of the tether 800 which allows the second end 804 of the tether 800 to have a width greater that the diameter of the opening 524, 698 of the container 502 or housing 690. In the collapsed configuration, the free end 812 of the aglet 806 may be biased towards the intermediate portion 808 of the tether 800 to reduce the outer profile thereof. This may allow the aglet 806 to be inserted through the housing stem 696 and into the interior of the housing 690 or through the stem 508 and into the interior 540 of the container 502. The aglet 806 may return to the expanded first configuration when the compressive force is released. In the expanded configuration, the aglet 806 has a width that is greater than the inner diameter of the stem 508 or the housing stem 696. Thus, once the second end 804 of the tether 800 is inserted into the interior of the housing 690, the aglet 806 of the tether 800 resists removal of the cap 514, 614 from the container 502 or housing 690. For example, the aglet 806 engages an inner surface of the container 502 or the housing 690 to resist removal of the cap 514, 614.

As will be appreciated, the lengths of irrigation, lens wash, gas supply, alternate gas supply tubing may have any suitable size (e.g., diameter). In addition, the sizing (e.g., diameters) of the tubing may vary depending on the application. In one non-limiting embodiment, the irrigation supply tubing may have an inner diameter of approximately 6.5 mm and an outer diameter of 9.7 mm. The lens wash supply tubing may have an inner diameter of approximately 5 mm and an outer diameter of 8 mm. The gas supply tubing may have an inner diameter of approximately 2 mm and an outer diameter of 3.5 mm. The alternative gas supply tubing may have an inner diameter of approximately 5 mm and an outer diameter of 8 mm.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

All apparatuses and methods discussed herein are examples of apparatuses and/or methods implemented in accordance with one or more principles of this disclosure. These examples are not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure.

In the foregoing description and the following claims, the following will be appreciated. The phrases "at least one", "one or more", and "and/or", as used herein, are open-ended expressions that are both conjunctive and disjunctive in operation. The term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The foregoing discussion has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. One skilled in the art will appreciate that the disclosure may be used with many modifications of structure, arrangement, proportions, materials, components, and otherwise, used in the practice of the disclosure, which are particularly adapted to specific environments and operative requirements without departing from the principles of the present disclosure. For example, elements shown as integrally formed may be constructed of multiple parts or elements shown as multiple parts may be integrally formed, the operation of elements may be reversed or otherwise varied, the size or dimensions of the elements may be varied, and features and components of various embodiments may be selectively combined. The presently disclosed embodiments are therefore to be considered in all respects as illustrative and not restrictive, the scope of the claimed invention being indicated by the appended claims, and not limited to the foregoing description.

The following claims are hereby incorporated into this Detailed Description by this reference, with each claim standing on its own as a separate embodiment of the present disclosure. In the claims, the term "comprises/comprising" does not exclude the presence of other elements or steps. Furthermore, although individually listed, a plurality of means, elements or method steps may be implemented by, e.g., a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second", etc., do not preclude a plurality. Reference signs in the claims are provided merely as a clarifying example and shall not be construed as limiting the scope of the claims in any way.

What is claimed is:

1. A reservoir arranged and configured to couple to an endoscope for use in an endoscopic procedure, the reservoir comprising:

a container configured to contain a fluid therein, the container extending from a first end to a second end and having a reduced diameter stem extending from the first end, the reduced diameter stem defining an opening for receiving a fluid;

a water outlet;

a gas inlet; and a port, the port comprising:

a sealing ring defining an aperture extending from a first end to a second of the sealing ring, the aperture in fluid communication with the opening in the container;

a cap positioned adjacent to the first end of the aperture of the sealing ring; and a biasing mechanism disposed between the container and the sealing ring.

2. The reservoir of claim 1, wherein the water outlet comprises a water supply tube including a first end, a second end, and a first lumen extending therethrough, wherein the first lumen is in fluid communication with a bottom portion of the container and the second end of the water supply tube is positioned external to the container; and wherein the gas inlet comprises a gas supply tube including a first end, a second end, and a second lumen extending therethrough, wherein the second lumen is in operative fluid communication with the container and the second end of the gas supply tube is positioned external to the container.

3. The reservoir of claim 1, wherein the biasing mechanism is configured to bias the sealing ring away from the first end of the container.

4. The reservoir of claim 1, wherein the sealing ring is movable between a first configuration configured to fluidly seal the opening in the container and a second configuration configured to provide a fluid path from external to the container and through the aperture of the sealing ring and the opening in the container.

5. The reservoir of claim 4, wherein when in the second configuration, the sealing ring is pressed towards the first end of the container.

6. The reservoir of claim 1, further comprising a tether extending between an interior of the container and the cap.

7. The reservoir of claim 1, wherein the biasing mechanism is configured to bias the sealing ring into the cap.

8. The reservoir of claim 1, wherein a diameter of the aperture of the sealing ring is substantially constant from the second end to an intermediate location and increases from the intermediate location to the first end to form a tapered first end region.

9. The reservoir of claim 8, wherein an outer diameter of the cap is tapered and configured to mate with the tapered first end region of the aperture of the sealing ring.

10. The reservoir of claim 1, further comprising an O-ring disposed between the sealing ring and the reduced diameter stem of the container.

11. A system comprising the reservoir of claim 1 and a filling bottle comprising a mouth, wherein the mouth is configured to engage a surface of the sealing ring along a perimeter lying beyond an outermost extent of the cap.

12. A reservoir arranged and configured to couple to an endoscope for use in an endoscopic procedure, the reservoir comprising:

a container configured to contain a fluid therein, the container extending from a first end to a second end and having a reduced diameter stem extending from the first end, the reduced diameter stem defining an opening for receiving a fluid;

a water inlet;

a gas inlet; and a port, the port comprising:

a sealing ring defining an aperture extending from a first end to a second of the sealing ring, the aperture in fluid communication with the opening in the container;

a cap positioned adjacent to the first end of the aperture of the sealing ring and configured to selectively form a fluid tight seal with the sealing ring; and a biasing mechanism disposed between the container and the sealing ring;

wherein the sealing ring is movable between a first closed configuration and a second open configuration.

13. The reservoir of claim 12, wherein when in the first closed configuration, the biasing mechanism is configured to bias the sealing ring against the cap.

14. The reservoir of claim 12, wherein when in the second open configuration, a force is exerted on the first end of the sealing ring to move the sealing ring away from the cap.

15. The reservoir of claim 12, further comprising a tether extending between an interior of the container and the cap.

16. The reservoir of claim 15, wherein the tether comprises a first end coupled to the cap and a second end disposed within the interior of the container.

17. The reservoir of claim 16, wherein the second end of the tether is deformable between a first expanded configuration and a second collapsed configuration.

18. The reservoir of claim 17, wherein when the second end of the tether is in the first expanded configuration, the second end of the of the tether has a width greater than a width of the opening in the container.

19. The reservoir of claim 17, wherein when the second end of the tether is in the second collapsed configuration, the second end of the of the tether has a width less than a width of the opening in the container.

* * * * *